United States Patent
Chan et al.

(10) Patent No.: US 9,518,298 B2
(45) Date of Patent: Dec. 13, 2016

(54) DACH1 AS A BIOMARKER FOR DIABETES

(71) Applicants: The Chinese University of Hong Kong, Shatin, N.T. (CN); Hospital Authority, Kowloon (CN)

(72) Inventors: Juliana Chung-Ngor Chan, Tai Po (CN); Wing-Yee So, Kowloon (CN); Ronald Ching-Wan Ma, Hong Kong (CN)

(73) Assignees: The Chinese University of Hong Kong, Shatin, N. T., Hong Kong SAR (CN); Hospital Authority, Kowloon, Hong Kong SAR (CN)

( * ) Notice: Subject to any disclaimer, the term of this patent is extended or adjusted under 35 U.S.C. 154(b) by 0 days.

(21) Appl. No.: 14/209,902

(22) Filed: Mar. 13, 2014

(65) Prior Publication Data

US 2014/0315198 A1    Oct. 23, 2014

Related U.S. Application Data

(63) Continuation of application No. 13/597,048, filed on Aug. 28, 2012, now abandoned.

(51) Int. Cl.
*C07H 21/04* (2006.01)
*C12Q 1/68* (2006.01)

(52) U.S. Cl.
CPC ........... *C12Q 1/6883* (2013.01); *C12Q 1/6886* (2013.01); *C12Q 2600/156* (2013.01); *C12Q 2600/178* (2013.01)

(58) Field of Classification Search
None
See application file for complete search history.

(56) References Cited

U.S. PATENT DOCUMENTS

2003/0092019 A1*  5/2003  Meyer et al. .................. 435/6

FOREIGN PATENT DOCUMENTS

WO            95/11995       5/1995

OTHER PUBLICATIONS

Pepe et al. (Am J. Epidemiology, 2004, vol. 159, pp. 882-890).*
Mummidi et al (Journal of Biological Chemistry 2000 vol. 275 No. 25 pp. 18946-18961).*
Juppner (Bone 1995 vol. 17 No. 2 Supplement 39S-42S).*
Ioannidis (Nature Genetics, vol. 29, pp. 306-309, Nov. 2001).*
Hirschhorn et al. (Genetics in Medicine. vol. 4, No. 2, pp. 45-61, Mar. 2002).*
Lusis et al. 2000 Nature vol. 407 p. 233.*
rs1408888 (ss24708289, entry date Aug. 10, 2004 NCBI dbSNP database).*
Griffen et al. (Tibtech Feb. 2000 vol. 18 p. 77).*
Olden et al. (AM J Kidney Dis 2013 vol. 6 p. 889).*
Dreja et al. (Diabetologia, vol. 53, pp. 309-320, 2010).*
Ng et al. (Blood, vol. 109, No. 3, pp. 916-925, Feb. 2007).*
Ma et al. (PLOS One, vol. 9, No. 1, e84770, Jan. 2014).*
Griffin et al., "Single-Nucleotide Polymorphism Analysis by MALDI-TOF Mass Spectrometry," TIBTCH Feb. 2000, vol. 18, 77-84.
Hirschhorn, et al., "A Comprehensive Review of Genetic Association Studies," Genetics in Medicine, Mar./Apr. 2002, vol. 4, No. 2, 45-61.
Ioannidis et al., "Why Most Published Research Findings are False," PLoS Medicine, Aug. 2005, vol. 2, Issue 8, 696-701.
Jüpper, "Functional Properties of the PTH/PTHrP Receptor," Bone, vol. 17, No. 2 Supplement, Aug. 1995, 39S-42S.
Lusis, "Atherosclerosis," Nature, vol. 407, Sep. 14, 2000, 233-241.
Mummidi et al., "Evolution of Human and Non-Human Primate CC Chemokine Receptor 5 Gene and mNRA," The Journal of Biological Chemistry, vol. 275, No. 25, Jun. 23, 2000, 18946-18961.
Olden et al., "Overlap Between Common Genetic Polymorphisms Underpinning Kidney Traits and Cardiovascular Disease Phenotypes: The CKDGen Consortium," Am J Kidney Dis. 2013;61(6) 889-898.
Pepe et al, "Limitations of the Odds Ratio in Gauging the Performance of a Diagnostic, Prognostic, or Screening Marker," Am. J. Epidemiology, 2004, vol. 159, 882-890.
RS1408888 (SS2209240 entry date Oct. 19, 2000 NCBI dbSNP database).

* cited by examiner

*Primary Examiner* — Jeanine A Goldberg
(74) *Attorney, Agent, or Firm* — Kilpatrick Townsend & Stockton LLP

(57) ABSTRACT

The present invention provides a method for assessing the presence and risk of developing type 2 diabetes or cardiovascular disease in a subject by detecting sequence variation in DACH1 (Dachshund homolog 1) gene. A kit and device useful for such a method are also provided. In addition, the present invention provides a method for treating type 2 diabetes or cardiovascular disease in patients who have been tested and shown to have the pertinent genetic variations.

11 Claims, 11 Drawing Sheets

A.

B.

ized, the number of individuals suffering from diabetes is
DACH1 AS A BIOMARKER FOR DIABETES REFERENCE TO A "SEQUENCE LISTING," A TABLE, OR A COMPUTER PROGRAM LISTING APPENDIX SUBMITTED AS AN ASCII TEXT FILE The Sequence Listing written in file -96-1.TXT, created on May 16, 2014, 8,192 bytes, machine format IBM-PC, MS-Windows operating system, is hereby incorporated by reference in its entirety for all purposes.

BACKGROUND OF THE INVENTION

Diabetes mellitus, often referred to simply as diabetes, encompasses a variety of conditions due to abnormal energy metabolism, characterized by chronic high blood glucose levels (hyperglycemia). Blood glucose levels are controlled by a complex network of chemicals and hormones in the human body. Since glucose is the main body fuel, there are many stress hormones which maintain blood glucose within a narrow range of 4-8 mmol/l by converting energy store (fat and glycogen) to glucose. On the other hand, insulin, produced by the beta cells of the pancreas, is the only hormone which can reduce blood glucose by promoting glucose uptake in the peripheral tissues. Thus, the abnormally high level of blood glucose in a person with diabetes is caused by defects in either insulin secretion or insulin action, attributable to a combination of hereditary, acquired, and environmental factors. Majority of diabetes are either type 1 diabetes, previously known as childhood-onset diabetes or insulin-dependent diabetes, or type 2 diabetes, previously known as adult-onset diabetes or non-insulin-independent diabetes.

Type 1 diabetes is characterized by loss of the insulin-producing beta cells of the islets of Langerhans in the pancreas, resulting in a deficiency of insulin production. The principal treatment for this type of diabetes is therefore delivery of artificial insulin, usually via injection. Type 2 diabetes (T2D) is more common than type 1 diabetes with over 90% of affected people having T2D. The latter is closely associated with modernization characterized by obesity and insulin resistance (reduced sensitivity to insulin action) although diminished insulin production is needed for development of overt hyperglycemia. Both twin and family studies support a strong genetic component for T2D. Recent genome wide association studies implicate multiple common genetic variants in the development of T2D although these factors only explained a small percentage of the variance of the genetic risk of T2D. Many of these variants are located in non-coding regions, suggesting that dysregulation of gene expression may play a pivotal role in complex diseases such as diabetes. Furthermore, there is strong evidence showing inter-ethnic differences in distribution and frequency of genetic or sequence variants for diabetes such that many of these variants discovered in Caucasian populations may not be applicable to Asian population. Apart from different developmental, environmental and cultural factors which can initiate, perpetuate and modify the clinical course, genomic architectural variations such as patterns of linkage disequilibrium (LD), recombination hotspots, insertion/deletion and copy number variations, DNA sensitive sites, regulatory regions for epigenetic phenomenon and fetal programming may all contribute to these inter-ethnic differences. See, e.g., Chan et al., *JAMA*, 2009. 301(20): p. 2129-40; Ramachandran et al., *Lancet*, 2010. 375(9712): p. 408-18.

Various factors are known to be indicative of a person's risk to develop T2D, most of them strongly influenced by the person's lifestyle, age, ethnic background, and family history. The presence of at least one, often more than one, of these risk factors, such as a body mass index (BMI) in the range of obesity (especially central obesity due to accumulation of excess visceral fat as indicated by large waist circumference), elevated blood glucose or insulin level (especially elevated fasting or post prandial blood glucose or insulin level), and reduced sensitivity to insulin, predisposes a person to the high likelihood of developing T2D, if no corrective measure is taken.

As people's living standards continue to improve globally, the number of individuals suffering from diabetes is also rapidly increasing. The World Health Organization (WHO) estimates that by 2030 the number of people living with diabetes will exceed 350 million worldwide. Due to the rising incidence of diabetes, its chronic nature without an ultimate cure, and serious health implications associated with its complications, including but not limited to cardiovascular disease, kidney failure, cancer, blindness, leg amputation, there exists an urgent need for new and effective means to assess or predict the risk of individuals who might later develop diabetic conditions, so that prophylactic measures can be taken to prevent or delay the onset of diabetes in these individuals or to reduce severity of the pertinent symptoms/risks associated with diabetes.

There are also clinical and experimental data showing that good glycemic control and use of certain drugs such as statins (which inhibit the HMG coA reductase), blockers of renin angiotensin system, and blood glucose lowering drugs including but not limited to insulin, sulphonylureas, metformin and glitazones, may reduce the risk of not only cardiovascular and renal diseases but also cancer (see, e.g., Yang et al., *Diabetes, Obesity and Metabolism* 2012 14:579-85; and Yang et al., *Diabetes Metab Res Rev* 2012; 28:379-87). These preventive measures are especially important in high risk subjects such as those who have additional risk factors for cardiovascular disease, e.g., positive family history of diabetes (suggesting the possibility of harboring other (epi)genetic factors yet to be identified), chronic kidney disease, chronic infection (e.g., hepatitis B and C) and a combination of low BMI (reflecting poor pancreatic beta cell reserve) and high waist circumference (reflecting increased visceral fat with insulin resistance) In these high risk subjects, detection of genetic risk factors before severe metabolic decompensation will help clinicians to intensify treatment in order to prevent metabolic deterioration and optimize metabolic control to reduce risk of cancer, cardiovascular and renal disease.

Because of the enormous social and economical impact the above discussed diseases impart globally, there exist clear and immediate needs to develop new and effective means for accurate diagnosis of these diseases or early assessment a patient's risk of developing these diseases in the future, such that early intervention may be performed to minimize the harmful effects associated with these diseases and/or the risk of developing the diseases. The present invention fulfills this and other related needs.

BRIEF SUMMARY OF THE INVENTION

In a first aspect, the present invention provides a method for assessing the presence or risk of type 2 diabetes (T2D), cardiovascular disease, or cancer in a subject. The method includes these steps: (a) performing an assay that determines nucleotide sequence of at least a portion of genomic sequence of DACH1 (Dachshund homolog 1) present in a biological sample taken from the subject; and (b) comparing the sequence determined in step (a) with a corresponding standard sequence of DACH1, wherein a variation in the sequence determined in step (a) when compared with the standard sequence indicates that the subject has or is at risk of developing T2D, cardiovascular disease, or cancer. In some embodiments, the relevant portion of DACH1 genomic sequence is determined by sequencing the DACH1 DNA sequence, e.g., following an amplification reaction such as polymerase chain reaction (PCR); in other embodiments, the DACH1 genomic sequence is determined by sequencing a transcript or RNA of the DACH1 genomic sequence, e.g., following a reverse transcriptase-polymerase chain reaction (RT-PCR).

In some cases, the sample is a blood or saliva sample. In some cases, the subject is an Asian descent. In some cases, the subject has a BMI greater than 27 kg/m$^2$ and/or (1) waist greater than 90 cm if the subject is a man; or (2) waist greater than 80 cm if the subject is a woman. In some cases, the subject has a BMI less than 20 kg/m$^2$. In some cases, the subject is younger than 20 years old. In some cases, the subject is diagnosed of diabetes before 40 years of age. In some cases, the subject has a family history of diabetes but has not been diagnosed of T2D. In some cases, the assay in step (a) comprises an amplification reaction, such as a polymerase chain reaction (PCR) or a reverse transcriptase-polymerase chain reaction (RT-PCR) when the DACH1 genomic sequence is determined by way of determining the polynucleotide sequence of its transcript, e.g., RNA sequence. One example of sequence variation is polymorphism rs1408888. In some cases, the assay in step (a) comprises mass spectrometry.

In some cases, after the subject is indicated as having developing T2D or cardiovascular disease or cancer, one or more treatment steps should be taken. For example, a physician may prescribe administering to the subject a cholesterol lowering drug or a blood glucose lowering drug. If cancer presence is confirmed, treatment plans such as surgical intervention, radiotherapy, and/or chemotherapy may be employed. On the other hand, the subject, once indicated as at risk of developing T2D or cardiovascular disease or cancer according to the methods described above, may receive one or more further steps of monitoring for any of these conditions on a regular basis, utilizing physical examination tools, laboratory tests and application of various scanning and/or scoping technologies to image high risk anatomical areas. Preventive steps may also be taken such as changing dietary habits, increasing physical activity level, etc.

In a second aspect, the present invention provides a kit for assessing the presence or risk of T2D or cardiovascular disease or cancer in a subject. The kit includes two oligonucleotide primers for specifically amplifying: (1) at least a segment of genomic sequence of DACH1 (Dachshund homolog 1); or (2) complement of (1), in an amplification reaction. Such an amplification reaction may be a polymerase chain reaction (PCR) such as RT-PCR. The kit typically further includes an instruction manual.

In a third aspect, the present invention provides a target for intervention including but not limited to use of molecular (e.g., microRNA, small interfering RNA, chromatin modifiers) and non-molecular (e.g., drugs and chemicals) tools to improve the expression and function beta cells. For instance, the SNP rs1408888 is a potential target for siRNA. This SNP is located in a highly conserved non-coding element, which is known to be implicated in pancreatic development.

DEFINITIONS

Figure 1:
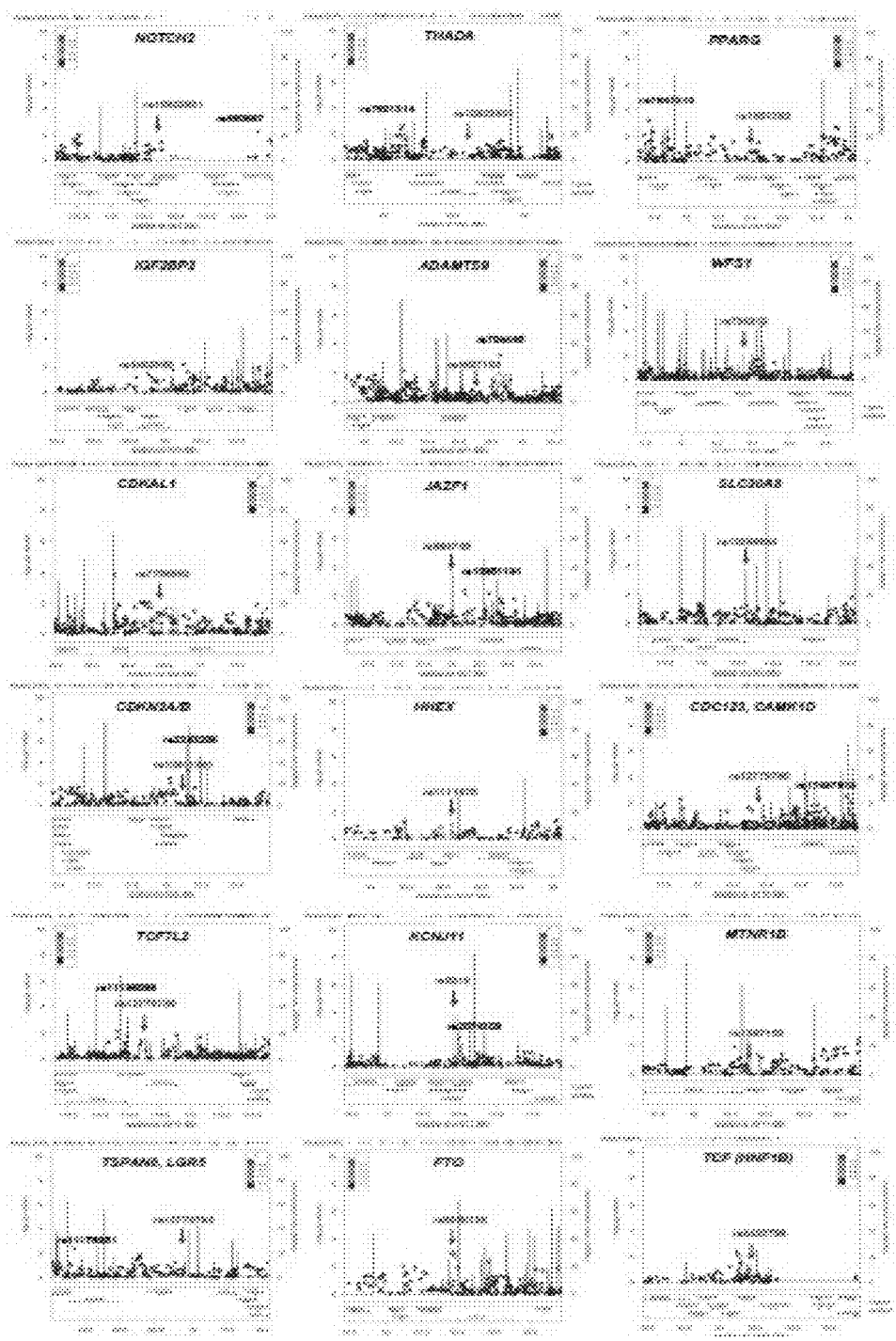
FIG. 1: Regional plots of previously reported T2D-associated regions. The $-\log_{10}$ P value for the allelic test from the stage 1 (genome scan) were plotted as a function of genomic position (NCBI build 36) for the following regions: (A) NOTCH2, (B) THADA, (C) PPARG, (D) IGF2BP2, (E) ADAMTS9, (F) WFS1, (G) CDKAL1, (H) JAZF1, (I) SLC30A8, (J) CDKN2AB, (K) HHEX, (L) CDC123/CAMK1D, (M) TCF7L2, (N) KCNJ11, (O) MTNR1B, (P) TSPAN8/LGR5, (Q) FTO, and (R) TCF (HNF1B). The reported SNPs in previous genome wide association studies (GWAS) were denoted by purple diamond. LD information (based on HapMap) was shown by color-coded points. Estimated recombination rate (the blue line) based on the Japanese and Chinese HapMap populations was plotted to reflect the local LD structure around the significant SNPs. Gene annotations were taken from NCBI Reference.

The term "type 2 diabetes" (T2D) refers to a metabolic disorder that is characterized by high blood glucose in the context of varying combinations of insulin resistance and insulin deficiency. Type 2 diabetes may be caused by a combination of lifestyle and genetic factors. Diabetes can be caused by distinct clinical entities such as endocrine disorders (e.g., Cushing's syndrome) and chronic pancreatitis. However, the majority of people with diabetes have risk factors including but not limited to obesity, hypertension, high blood cholesterol, metabolic syndrome (high triglyceride, low HDL-C, high blood glucose, high blood pressure, large waist), which may share common metabolic pathways, further amplified by aging, energy dense diets (e.g., high-fat and high glucose), sedentary lifestyle and use of certain drugs (e.g., beta blockers, steroids). On the other hand, having relatives (especially first degree) with T2D increases risks of developing T2D substantially. Symptoms of T2D often include polyuria (frequent urination), polydipsia (increased thirst), polyphagia (increased hunger), fatigue, and weight loss. The abnormal neurohormonal and metabolic milieu characterized by hyperglycemia, dyslipidemia and low grade inflammation can trigger a cascade of signaling pathways, which can lead to cell death and dysregulated cell growth, giving rise to multiple morbidities including heart disease, strokes, limb amputation, visual loss, kidney failure, cancers, and cognitive impairment.

The term "cardiovascular disease" refers to a broad class of diseases that involve the heart or blood vessels (arteries and veins) and affect the cardiovascular system, such as conditions related to atherosclerosis (arterial disease). These include but not limited to stroke, coronary heart disease and peripheral vascular disease. Known risk factors for cardiovascular diseases include unhealthy eating, lack of exercise, obesity, suboptimally managed diabetes, abnormal blood lipids, high blood pressure, excessive consumption of alcohol, use of tobacco, as well as genetic background.

As used herein, the term "body mass index" or "BMI" refers to a number calculated from a person's weight and height to reflect the "fatness" or "thinness" of a person. More specifically, BMI=mass (kg)/(height (m))$^2$ or mass (lb)×703/(height (in))$^2$. Typically, in Caucasian populations, a BMI of 20 to 25 kg/m$^2$ is considered optimal weight; a BMI lower than 20 kg/m$^2$ suggests the person is underweight whereas a BMI above 25 kg/m$^2$ may indicate the person is overweight; a BMI above 30 kg/m$^2$ suggests the person is obese; and a BMI over 40 kg/m$^2$ indicates the person to be morbidly obese. Compared to Caucasians, Asians have more body fat for the same degree of BMI and waist circumference. Thus, normal weight and obesity in Asians are defined as <23 kg/m$^2$ and ≥25 kg/m$^2$ respectively. While high BMI may predict risk for diabetes or prediabetes, people with low BMI, which correlates with beta cell function, are also at high risk, especially if these subjects develop central obesity, which tends to be associated with insulin resistance or reduced insulin sensitivity.

In this disclosure, the term "biological sample" or "sample" includes any section of tissue or bodily fluid taken from a test subject such as a biopsy and autopsy sample, and frozen section taken for histologic purposes, or processed forms of any of such samples. Biological samples include blood and blood fractions or products (e.g., serum, plasma, platelets, white blood cells, red blood cells, and the like), sputum or saliva, lymph and tongue tissue, cultured cells, e.g., primary cultures, explants, and transformed cells, stool, urine, stomach biopsy tissue etc. A biological sample is typically obtained from a eukaryotic organism, which may be a mammal, may be a primate and may be a human subject.

In this disclosure, the term "biopsy" refers to the process of removing a tissue sample for diagnostic or prognostic evaluation, and to the tissue specimen itself. Any biopsy technique known in the art can be applied to the methods of the present invention. The biopsy technique applied will depend on the tissue type to be evaluated (e.g., tongue, colon, prostate, kidney, bladder, lymph node, liver, bone marrow, blood cell, stomach tissue, etc.) among other factors. Representative biopsy techniques include, but are not limited to, excisional biopsy, incisional biopsy, needle biopsy, surgical biopsy, and bone marrow biopsy and may comprise endoscopy such as colonoscopy. A wide range of biopsy techniques are well known to those skilled in the art who will choose between them and implement them with minimal experimentation.

In this disclosure, the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by a polymerase chain reaction or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamine) containing restriction-digested genomic DNA, is not an "isolated" nucleic acid.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription and/or translation of the gene product and the regulation of the transcription and/or translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refer to chemical compounds that have a structure that is different from the general chemical structure of an amino acid, but that functions in a manner similar to a naturally occurring amino acid.

Amino acids may include those having non-naturally occurring D-chirality, as disclosed in WO01/12654, which may improve the stability (e.g., half-life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains.

The term "antibody" also refers to antigen- and epitope-binding fragments of antibodies, e.g., Fab fragments, that can be used in immunological affinity assays. There are a number of well characterized antibody fragments. Thus, for example, pepsin digests an antibody C-terminal to the disulfide linkages in the hinge region to produce F(ab)'$_2$, a dimer of Fab which itself is a light chain joined to $V_H$-$C_H$1 by a disulfide bond. The F(ab)'$_2$ can be reduced under mild conditions to break the disulfide linkage in the hinge region thereby converting the (Fab')$_2$ dimer into an Fab' monomer. The Fab' monomer is essentially a Fab with part of the hinge region (see, e.g., Fundamental Immunology, Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody also includes antibody fragments either produced by the modification of whole antibodies or synthesized using recombinant DNA methodologies.

The phrase "specifically binds," when used in the context of describing a binding relationship of a particular molecule to a protein or peptide, refers to a binding reaction that is determinative of the presence of the protein in a heterogeneous population of proteins and other biologics. Thus, under designated binding assay conditions, the specified binding agent (e.g., an antibody) binds to a particular protein at least two times the background and does not substantially bind in a significant amount to other proteins present in the sample. Specific binding of an antibody under such conditions may require an antibody that is selected for its specificity for a particular protein or a protein but not its similar "sister" proteins. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective binding reaction will be at least twice background signal or noise and more typically more than 10 to 100 times background. On the other hand, the term "specifically bind" when used in the context of referring to a polynucleotide sequence forming a double-stranded complex with another polynucleotide sequence describes "polynucleotide hybridization" based on the Watson-Crick base-pairing, as provided in the definition for the term "polynucleotide hybridization method."

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, and in situ hybridization.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the cDNA or genomic sequence for human DACH1 (Dachshund homolog 1) gene or a portion thereof. Typically, at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. In this disclosure the term "primer pair" means a pair of primers that hybridize to opposite strands a target DNA molecule or to regions of the target DNA which flank a nucleotide sequence to be amplified. In this disclosure, the term "primer site" means the area of the target DNA or other nucleic acid to which a primer hybridizes.

A "label," "detectable label," or "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a probe or a molecule with defined binding characteristics (e.g., a polypeptide with a known binding specificity or a polynucleotide), so as to allow the presence of the probe (and therefore its binding target) to be readily detectable.

A "standard sequence" as used herein refers to the polynucleotide sequence of a predetermined genomic DNA segment, e.g., a defined portion or the entire length of a human genomic sequence of a given gene, such as the human Dachshund homolog 1 (DACH1) genomic sequence, including 2 kb upstream and 2 kb downstream flanking sequences, that is present in a publically accessible database, e.g., the University of California Santa Cruz database (hg18), as the standard human genomic sequence for that particular gene. When a genomic DNA sequence determined from a test sample is compared with a "standard sequence," the test sequence is aligned with the "standard sequence" at the corresponding nucleotide bases of the genomic sequence to reveal any sequence variation. For this particular application, the standard genomic sequence for human DACH1 gene (including some isoforms) is provided as below. In *Drosophila* insulin-producing cells, the *Drosophila* counterpart of DACH1 (dac) interacts physically to Pax6 to regulate the expression of insulin-like peptides dilp5.

| DACH1 isoforms Description | Transcript | length (nt) | peptide | length (aa) |
|---|---|---|---|---|
| DACH1 isoform c | NM 004392.5 | 4640 | NP 004383.3 | 506 |
| DACH1 isoform a | NM 080759.4 | 5246 | NP 542937.2 | 708 |
| DACH1 isoform b | NM 80760.4 | 4802 | NP 542938.2 | 560 |

| Gene | Entrez Gene ID | Description | Chr. | Cytoband | Strand | hg18 Start (bp) | hg18 End (bp) | hg18 2Kb upstream (promoter) | hg18 2Kb downstream (3'flanking) |
|---|---|---|---|---|---|---|---|---|---|
| DACH1 | 1602 | Dachshund homolog 1 (*Drosophila*) | 13 | 13q22 | − | 70910099 | 71339331 | 71339332-71341331 | 70908099-70910098 |
| DACH2 | 117154 | Dachshund homolog 2 (*Drosophila*) | X | Xq21.3 | + | 85290281 | 85974245 | 85288281-85290280 | 85974246-85976245 |
| PAX6 | 5080 | Paired box 6 | 11 | 11p13 | − | 31762916 | 31796085 | 31796086-31798085 | 31760916-31796085 |

The term "amount" as used in this application refers to the quantity of a polynucleotide of interest or a polypeptide of interest present in a sample. Such quantity may be expressed in the absolute terms, i.e., the total quantity of the polynucleotide or polypeptide in the sample, or in the relative terms, i.e., the concentration of the polynucleotide or polypeptide in the sample.

The term "effective amount" as used herein refers to an amount of a given substance that is sufficient in quantity to produce a desired effect. For example, an effective amount of a cholesterol lowering drug or a blood glucose lowering drug is the amount of said drug to achieve a decreased level of cholesterol or blood glucose, respectively, in a patient who has been given the drug for therapeutic purposes. An amount adequate to accomplish this is defined as the "therapeutically effective dose." The dosing range varies with the nature of the therapeutic agent being administered and other factors such as the route of administration and the severity of a patient's condition.

The term "subject" or "subject in need of treatment," as used herein, includes individuals who seek medical attention due to risk of, or actual suffering from T2D, cancer, or cardiovascular disease. Subjects also include individuals currently undergoing therapy that seek manipulation of the therapeutic regimen. Subjects or individuals in need of treatment include those that demonstrate symptoms of T2D or cardiovascular disease, or are at risk of suffering from T2D or cardiovascular disease or related symptoms. For example, a subject in need of treatment includes individuals with a genetic predisposition or family history for T2D, cancer, or cardiovascular disease, those who have suffered relevant symptoms in the past, those who have been exposed to a triggering substance or event, as well as those suffering from chronic or acute symptoms of the condition. A "subject in need of treatment" may be at any age of life.

DETAILED DESCRIPTION OF THE INVENTION

I. Introduction

The present inventors discovered for the first time the correlation between genomic sequence variation in the human Dachshund homolog 1 (DACH1) genomic sequence and medical conditions such as T2D and cardiovascular disease in human subjects. This discovery allows medical professionals to identify subjects at risk cardiovascular disease in a patient with T2D or assess the risk of developing T2D and cardiovascular disease in a subject at risk by studying the subject's DACH1 genomic sequence and then comparing the subject's sequence with a standard DACH1 genomic sequence that has been determined as a part of the standard human genome. Detection of such sequence variation(s) indicates the presence or elevated risk of developing T2D or cardiovascular disease in the subject. The detection of pertinent genomic sequence variation(s) can further guide physicians to devise or modify treatment plans for a subject in both prevention and therapeutic measures.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of interest used in this invention, e.g., the polynucleotide sequence of the human DACH1 gene, and synthetic oligonucleotides (e.g., primers) can be verified using, e.g., the chain termination method for sequencing double-stranded templates of Wallace et al., *Gene* 16: 21-26 (1981).

III. Acquisition of Biological Samples and Analysis of Genomic DNA Sequence

The present invention relates to determining at least a portion of the genomic sequence of a pertinent gene, such as the human DACH1 gene and/or its transcripts, found in a biological sample taken from a person being tested, as a means to detect the presence and/or to assess the risk of developing T2D, cancer, or cardiovascular disease in that person. Thus, the first steps of practicing this invention are to obtain a biological sample (e.g., tissue or bodily fluid sample) from a test subject and extract genomic DNA or RNA from the sample.

A. Acquisition and Preparation of Samples

A biological sample is obtained from a person to be tested or assessed for risk of developing T2D, cancer, or cardiovascular disease using a method of the present invention. Collection of a tissue or fluid sample from an individual is performed in accordance with the standard protocol laboratories, hospitals or clinics generally follow, such as during a biopsy, blood drawing, saliva collection, or oral swab. An appropriate amount of sample is collected and may be stored according to standard procedures prior to further preparation.

The analysis of genomic DNA found in a subject's sample according to the present invention may be performed using essentially any tissue or bodily fluid, so long as genomic DNA is expected to be present in such sample. The methods for preparing tissue or fluid samples for nucleic acid extraction are well known among those of skill in the art. For example, a subject's epithelial tissue sample should be first treated to disrupt cellular membrane so as to release nucleic acids contained within the cells.

B. Determination of Genomic Sequence

Possible sequence variation within a segment of a pertinent gene (such as the DACH1 gene), or one or more of its transcripts, is investigated to provide indication as to whether a test subject is suffering from T2D and/or cardiovascular disease, or whether the subject is at risk of developing T2D and/or cardiovascular disease in the future.

Typically a segment of the genomic sequence of an appropriate length is selected for sequencing analysis. The segment may be chosen from the genomic sequence of a pertinent gene defined by the same boundaries defining the gene's cDNA sequence, plus about 2,000 base pairs upstream and downstream from the boundaries. The length of the genomic sequence being analyzed is usually at least 15 or 20 contiguous nucleotides, and may be longer with at least 25, 30, 50, 100, 200, 300, 400, or more contiguous nucleotides.

1. DNA Extraction and Treatment

Methods for extracting DNA from a biological sample are well known and routinely practiced in the art of molecular biology, see, e.g., Sambrook and Russell, supra. RNA contamination should be eliminated to avoid interference with DNA analysis. Optionally, other components (such as proteins and lipids) may be removed from the biological sample prior to further analysis of the genomic DNA.

2. Optional Amplification and Sequence Analysis

Following the desired processing of DNA/RNA in a biological sample, the DNA/RNA is then subjected to sequence-based analysis, such that the genomic sequence of one or more of the pertinent genes, or one or more of its transcripts, found in a test subject may be determined and then compared with a standard sequence to detect any possible sequence variation. An amplification reaction is optional prior to the sequence analysis. A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., *PCR Protocols: A Guide to Methods and*

*Applications*, Academic Press, Inc. N.Y., 1990. PCR reagents and protocols are also available from commercial vendors, such as Roche Molecular Systems.

Although PCR amplification is typically used in practicing the present invention, one of skill in the art will recognize that amplification of the relevant genomic sequence may be accomplished by any known method, such as the ligase chain reaction (LCR), transcription-mediated amplification, and self-sustained sequence replication or nucleic acid sequence-based amplification (NASBA), each of which provides sufficient amplification.

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for determining the polynucleotide sequence of a genomic DNA for practicing the methods of the present invention include but are not limited to mass spectrometry, primer extension, polynucleotide hybridization, real-time PCR, melting curve analysis, high resolution melting analysis, heteroduplex analysis, pyrosequencing, and electrophoresis.

3. Determining Genomic DNA Sequence Variation Based on RNA Sequence Variation

As an alternative, genomic DNA sequence variations may also be detected by way of analyzing RNA sequences transcribed from the pertinent DNA sequences, which may include portion of the coding sequence or non-coding sequence of a gene of interest (e.g., DACH1). Methods for RNA extraction from a biological sample, sequence analysis of RNA or DNA molecules, optionally involving amplification techniques such as reverse transcription based amplification processes, e.g., RT-PCR, are well known in the art. Suitable samples for RNA sequence analysis may include peripheral blood monocytes (PBMC, see FIG. 3B) and specific tissue samples such as fat and muscles.

IV. Corresponding Standard Sequence

In order to practice the method of this invention, the standard genomic sequence(s) for one or more pertinent genes, such as the human DACH1 gene and its isoforms, will be chosen before the comparison with a test subject's genomic sequence of the corresponding gene at the corresponding location may be performed. In addition, genes closely related to or known to interact with DACH1 are included for possible testing.

1. Additional Genes that May Interact with DACH1

DACH1 does not belong to a specific KEGG pathway (http://www.genome.jp/dbget-bin/www_bget?hsa:1602). DACH1 contains two homologous protein domains, the Ski-Sno domain and the Macoilin domain. The Ski-Sno family contains a presumed domain that is about 100 amino acids long. All members of this family contain a conserved CLPQ motif. The c-ski proto-oncogene has been shown to influence proliferation, morphological transformation and myogenic differentiation. Sno, a Ski proto-oncogene homologue, is expressed in two isoforms and plays a role in the response to proliferation stimuli. DACH1 also contains this domain. It is involved in various aspects of development. Ski, Sno and DACH1 can all interact with Smad proteins to modify the activity of the TGFβ signaling pathway. In terms of GO (Gene Ontology) classifications, DACH1 is included in 11 GO categories.

TABLE 1

List of GO terms for DACH1

| Accession | Term | Ontology | No. Genes |
|---|---|---|---|
| GO:0007275 | multicellular organismal development | biological process | 36493 |
| GO:0030336 | negative regulation of cell migration | biological process | 676 |
| GO:0010944 | negative regulation of transcription by competitive promoter binding | biological process | 43 |
| GO:0006355 | regulation of transcription, DNA dependent | biological process | 31116 |
| GO:0000122 | negative regulation of transcription from RNA polymerase II promoter | biological process | 3177 |
| GO:0005634 | nucleus | cellular component | 58353 |
| GO:0005730 | nucleolus | cellular component | 5462 |
| GO:0000166 | nucleotide binding | molecular function | 55994 |
| GO:0005515 | protein binding | molecular function | 49291 |
| GO:0003677 | DNA binding | molecular function | 30704 |
| GO:0001078 | RNA polymerase II core promoter proximal region sequence-specific DNA binding transcription factor activity involved in negative regulation of transcription | molecular function | 198 |

2. Known Protein-Protein Interactions of DACH1:

In breast cancer cells, DACH1 binds and inhibit the function of estrogen receptor ERα (Popov et al., *Cancer Res,*

| DACH1 isoforms Description | Transcript | length (nt) | peptide | length (aa) |
|---|---|---|---|---|
| DACH1 isoform c | NM 004392.5 | 4640 | NP 004383.3 | 506 |
| DACH1 isoform a | NM 080759.4 | 5246 | NP 542937.2 | 708 |
| DACH1 isoform b | NM 80760.4 | 4802 | NP 542938.2 | 560 |

| Gene | Entrez Gene ID | Description | Chr. | Cytoband | Strand | hg18 Start (bp) | hg18 End (bp) | hg18 2Kb upstream (promoter) | hg18 2Kb downstream (3'flanking) |
|---|---|---|---|---|---|---|---|---|---|
| DACH1 | 1602 | Dachshund homolog 1 (*Drosophila*) | 13 | 13q22 | − | 70910099 | 71339331 | 71339332-71341331 | 70908099-70910098 |
| DACH2 | 117154 | Dachshund homolog 2 (*Drosophila*) | X | Xq21.3 | + | 85290281 | 85974245 | 85288281-85290280 | 85974246-85976245 |
| PAX6 | 5080 | Paired box 6 | 11 | 11p13 | − | 31762916 | 31796085 | 31796086-31798085 | 31760916-31796085 |

2009. 69(14):5752-5760). In stromal/preosteoblast cells, FGF-2 stimulates heat shock factor 2 (HSF-2) binding to DACH1 (Sundaram et al., *J Cell Biochem*, 2008. 103(6): 1747-1759). In cultured cells, DACH1 can bind to Smad4 to inhibit TGFβ signaling (Wu et al., *J Biol Chem*, 2003. 278(51):51673-51684). DACH1 binds to specific DNA sequences and recruit transcription elongation regulator-1 (TCERG1) to repress gene expression through interaction between the carboxy terminus of DACH1 and the FF2 domain of TCERG (Zhou et al., *J Biol Chem*, 2012. 285 (51):40342-40350). In *Drosophila* insulin-producing cells, the *Drosophila* counter part of DACH1 (dac) interacts physically with PAX6 to regulate the expression of insulin-like peptides dilp5 (Okamoto et al., *Proc Natl Acad Sci USA*, 2012. 109(7): p. 2406-2411).

V. Therapeutic and Preventive Measures

By illustrating the correlation between genomic sequence variation in one or more of the specific genes named above and the presence or heightened risk of developing T2D or cardiovascular diseases among subjects having such variation, especially those fitting certain profiles, such as those of Asian descent, younger than 20 years of age, and/or with extremes of BMI (e.g., less than 20 kg/m$^2$ or greater than 30 kg/m$^2$), the present inventors have provided a valuable tool for clinicians to determine, often in combination with other information and diagnostic or predictive or screening test results, how a subject having certain genomic sequence variation(s) should be monitored and/or treated for T2D and/or cardiovascular disease such that the symptoms of these conditions may be prevented, eliminated, ameliorated, reduced in severity and/or frequency, or delayed in their onset. For example, a physician may arrange for regular monitoring of various symptoms of T2D or cardiovascular diseases in a subject who has been deemed by the method of the present invention to have an elevated risk of developing T2D. The physician may also prescribe both pharmacological and non-pharmacological treatments such as lifestyle modification (e.g., reduce body weight by 5%, high fiber diet, walking for at least 150 minutes weekly) and medicines known to reduce risk of onset of diabetes (e.g., metformin, alpha glucosidase inhibitors, lipase inhibitors) to a subject who has been deemed by the method of the present invention to have an elevated risk of developing T2D. For a subject who has been deemed by the method of the present invention to suffer from or at risk of developing cardiovascular disease, the attending physician may prescribe medications to control risk factors such as high levels of blood cholesterol and triglycerol (e.g., statins and fibrates) and reduce angiotensin II activity (e.g., Angiotensin converting enzyme inhibitor (ACEI) and angiotensin II receptor blocker (ARB)), as well as place the subject under regular testing and monitoring of coronary artery condition.

VI. Kits and Devices

The present invention provides compositions and kits for practicing the methods described herein to detect possible genomic sequence variation of certain gene(s) and the transcripts thereof in a subject, which can be used for various purposes such as detecting or diagnosing the presence of T2D and/or cardiovascular disease in a subject, determining the risk of developing T2D and/or cardiovascular disease in a subject, and guiding the treatment plan for these conditions in the subject.

Kits for carrying out assays for determining the nucleotide sequence of a relevant genomic sequence typically include at least one oligonucleotide useful for specific hybridization with a predetermined segment of a pertinent genomic sequence (e.g., human DACH1 genomic sequence). Optionally, this oligonucleotide is labeled with a detectable moiety.

In some cases, the oligonucleotide specifically hybridizes with the standard sequence only but not with any of the variant sequences. In other cases, the oligonucleotide specifically hybridizes with one particular version of the variant sequence but not with other versions, nor with the standard sequence.

In some cases, the kits may include at least two oligonucleotide primers that can be used in the amplification of at least one segment of the genomic sequence of one pertinent gene (such as the DACH1 gene) or transcripts thereof by PCR. In some examples, at least one of the oligonucleotide primers is designed to anneal only to the standard sequence or only to a particular version of the variant sequences.

In addition, the kits of this invention may provide instruction manuals (e.g., internet-based decision support tools) to guide users in analyzing test samples and assessing the presence or future risk of T2D and/or cardiovascular disease in a test subject.

Furthermore, the present invention can also be embodied in a device or a system comprising one or more such devices, which is capable of carrying out all or some of the method steps described herein. For instance, in some cases, the device or system performs the following steps upon receiving a biological sample taken from a subject being tested for detecting T2D or cardiovascular disease, assessing the risk of developing T2D or cardiovascular disease, or guiding treatment of a subject having or at risk of developing any one of these conditions: (a) determining in the sample the nucleotide sequence of a pertinent genomic DNA segment or its transcript; (b) comparing the sequence determined from the sample with a corresponding standard sequence; and (c) providing an output indicating whether T2D or cardiovascular disease is present in the subject or whether the subject is at risk of developing T2D or cardiovascular disease. In other cases, the device or system of the invention performs the task of steps (b) and (c), after step (a) has been performed and the genomic sequence determined from (a) has been entered into the device. Preferably, the device or system is partially or fully automated.

EXAMPLES

The following examples are provided by way of illustration only and not by way of limitation. Those of skill in the art will readily recognize a variety of non-critical parameters that could be changed or modified to yield essentially the same or similar results.

Example 1

DACH1 as a Genetic Factor in Familiar Young-Onset Diabetes and Cardiovascular Disease in Chinese Population In an adequately powered genome-wide association study to detect common variants with moderate effect size applied to 99 Chinese obese subjects with familial young-onset T2D and 101 control subjects, the T allele of rs1408888 located in intron 1 of DACH1 was associated with an odds ratio (OR) of 2.49 (P=8.4×10$^{-5}$), with replication of OR of 1.07 (P=0.0112) in a meta-analysis of multi-ethnic Asian populations (7370 cases versus 7802 controls). In Chinese control subjects (n=599), the T allele of rs1408888 was associated with systolic blood pressure and insulin resistance (HOMA-IR). In a prospective cohort of 4296 Chinese T2D patients followed up for 8.3±3.4 years, 582 developed cardiovascular diseases (CVD) with T allele conferring a hazard ratio of 1.49 (P=0.0451) independent of conventional risk factors and treatments. Using autopsy samples of non-diabetic cases, the TT genotype of rs1408888 (n=173) was associated with coronary arteriosclerosis (OR=3.72, P=0.0184) and cardiovascular disease (CVD) (OR=2.2, P=0.0489) compared to TG/GG genotype carriers (n=173). Bioinformatics analysis confirmed the important role of DACH1 in developmental biology with rs1408888 falling within a highly conserved region subject to chromatin modification in islets with binding sites for multiple transcription factors. This consistent evidence supports a pathogenetic role of DACH1 for T2D and CVD with an intermediate phenotype of obesity and insulin resistance in Chinese populations.

Introduction

There is an epidemic of T2D in Asia with the most rapid increase in the young to middle-aged population (Chan et al., *JAMA*, 2009. 301(20): p. 2129-40; Ramachandran et al., *Lancet*, 2010. 375(9712): p. 408-18; Yang et al., *N Engl J Med*, 2010. 362(12): p. 1090-101). Chinese subjects with young-onset diabetes are characterized by strong family history, lack of auto-immune markers, obesity, cardiometabolic risk factors and predisposition to beta-cell dysfunction (Chan et al., 2009 supra; Ng et al., *Diabetes Care*, 2001. 24(4): p. 663-71; Pan et al., *Diabet Med*, 2004. 21(9): p. 1007-13; Thai et al., *Diabetes Res Clin Pract*, 2008. 80(2): p. 224-30). The combination of long disease duration and co-occurrence of multiple risk factors put these subjects at high risk for cardiovascular and renal disease with premature mortality (Hillier and Pedula, *Diabetes Care*, 2003. 26(11): p. 2999-3005; Pavkov et al., *JAMA*, 2006. 296(4): p. 421-6; Song and Hardisty, *QJM*, 2009. 102(11): p. 799-806; Yang et al., *Diabetes, Obesity and Metabolism* 2012 14:579-85; Yang et al., *Diabetes Metab Res Rev* 2012; 28:379-87).

Genome-wide association studies (GWAS) in Europeans have discovered more than 60 genetic regions associated with risk of T2D (Bonnefond et al., *Trends Mol Med*, 2010. 16(9): p. 407-16; Voight et al., *Nat Genet*, 2010. 42(7): p. 579-89). Although most regions have been replicated in Asian populations, there were significant inter-ethnic differences in allele frequency and effect size (Ramachandran et al., 2010 supra, Ng et al., *Diabetes*, 2008. 57(8): p. 2226-33). Subsequent GWAS in Japanese and Chinese populations have discovered additional loci associated with T2D, with the KCNQ1 region being replicated in other populations (Shu et al., *PLoS Genet*, 2010. 6(9); Tsai et al., *PLoS Genet*, 2010. 6(2): p. e1000847; Yamauchi et al., *Nat Genet*, 2010. 42(10): p. 864-8; Yasuda et al., *Nat Genet*, 2008. 40(9): p. 1092-7). The majority of these loci are related to beta-cell function with only a few linked to insulin resistance (Bonnefond et al., 2010 supra; Voight et al., 2010 supra).

In the Hong Kong Family Diabetes Study (HKFDS), the present inventors have reported the strong heritability of diabetes and obesity (Li et al., *Diabetes Metab Res Rev*, 2006. 22(1): p. 46-52), further supported by co-linkage of diabetes and cardio-metabolic traits to various chromosomal regions on linkage analysis (Ng et al., *Diabetes*, 2004. 53(10): p. 2676-83; Tam et al., *BMC Genet*, 2010. 11: p. 14). In a multi-staged experiment, the inventors discovered risk association of an intronic single nucleotide polymorphism (T) of rs1408888 in DACH1 (Dachshund homolog 1) in a GWAS adequately powered to detect moderate effect size for common variants applied to a carefully selected case-control cohort consisting of obese Chinese subjects with familial young-onset T2D. This variant was further validated in a meta-analysis of case-control cohorts of Asian populations. In Chinese healthy adults, the risk-conferring DACH1 genotype was associated with increased blood pressure and insulin resistance. In a large prospective cohort of Chinese T2D patients and using autopsy samples in non-diabetic subjects, the risk allele was associated with increased risk of cardiovascular disease and related death as well as pathological features of coronary and pancreatic arteriosclerosis. Bioinformatics analysis supported the important role of DACH1 in developmental biology with the putative variant falling within the vicinity of a conserved non-coding element (CNE) subject to chromatin modification with multiple binding sites. This consistent evidence suggests a possible pathogenetic role of DACH1 in T2D and cardiovascular disease with obesity and insulin resistance intermediate phenotypes in Chinese populations.

Results

Associations with T2D Signals Reported in GWAS or Candidate Gene Studies

The inventors first examined the GWAS signals associated with T2D risk in Europeans (Voight et al., 2010 supra; Saxena et al., *Science*, 2007. 316(5829): p. 1331-6; Zeggini et al., *Science*, 2007. 316(5829): p. 1336-41) using their GWAS dataset. FIG. 1 shows results of in silico replication of confirmed SNPs of 18 T2D genes or proxy SNPs in high LD ($r^2$>0.6 based on Hapmap CHB+JPT population data) for SNPs not available in our dataset. The T allele of CDKN2A/B rs2383208 ($r^2$=0.98 with rs10811661) and A-allele of FTO rs8050136 were significantly associated with T2D (P<0.05) while the risk alleles for KCNJ11, CDKAL1, HHEX, IGF2BP2, ADAMTS9 and WFS1 trended towards the same direction as reported in European studies (P>0.05).

Associations with Familial Young-Onset T2D in GWAS

Figure 2:
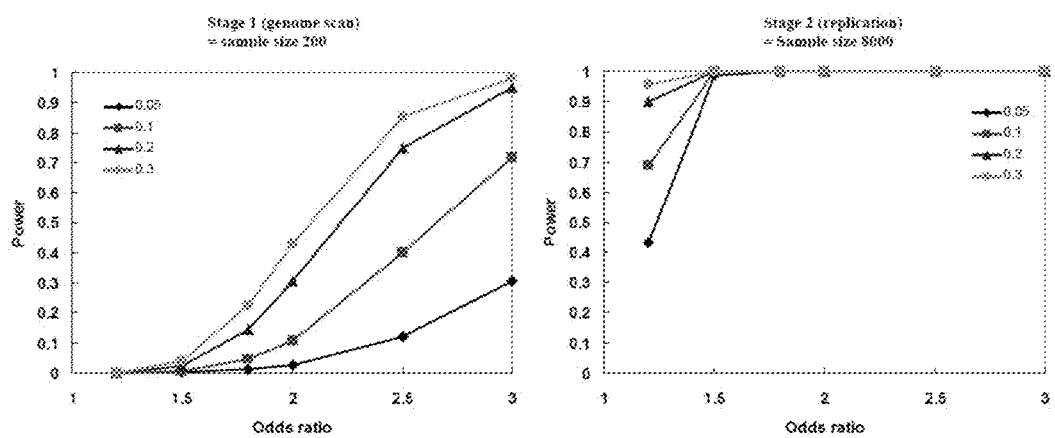
FIG. 2: Power calculation of the study. Assuming an additive model with allele frequencies ranging from 0.05 to 0.30 (0.05, black; 0.1, red; 0.2, blue; 0.3, green), study powers were estimated for detecting T2D risk with an odds ratio ranging from 1.2 to 3 for under the prevalence of 0.1, at the α level of $1 \times 10^{-4}$ in stage 1 (left, genome scan) and that of 0.05 in stage 2 (right, replication), respectively.
Figure 3:
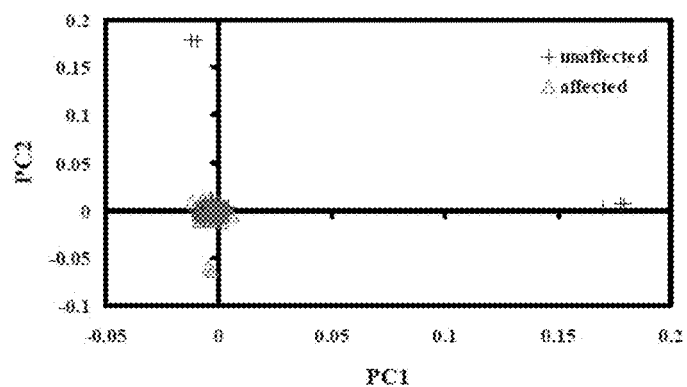
FIG. 3: A. Multidimensional scaling analysis (MDS) plot for checking population stratification between 99 T2D patients and 101 controls in the genome-wide association study. The MDS plot shows the first two principal components (PC), based on genotype data from stage 1 (genome scan) of the present study. B. Expression of DACH1 in PBMC was detected by quantitative real-time PCR in 65 control and 63 samples of type 2 diabetes mellitus (DM). Expression level was normalized to the expression of β actin using the ΔΔCt method. The results are represented as mean±standard error of the mean (SEM).
Figure 3:
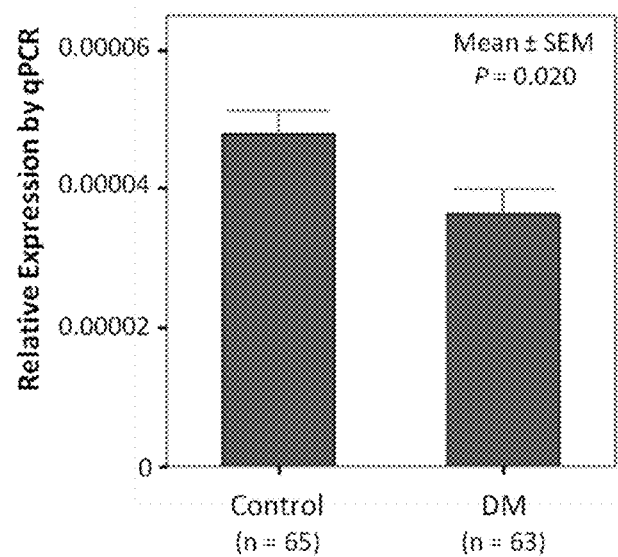
Figure 4:
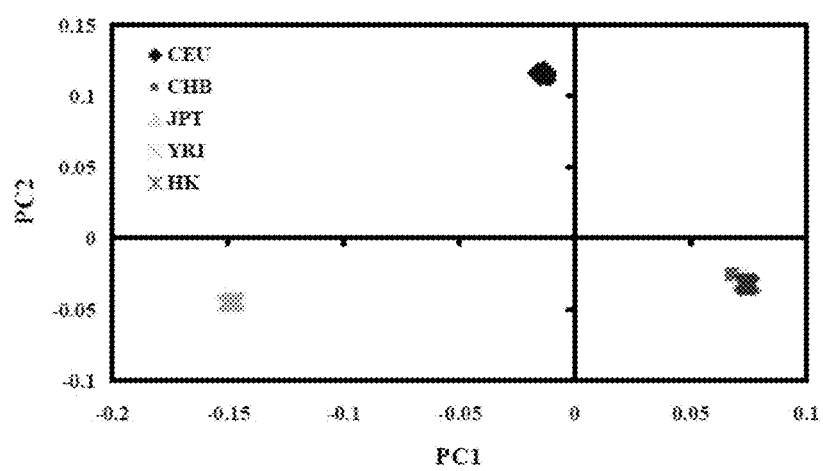
FIG. 4: Multidimensional scaling analysis (MDS) plot. The MDS plot shows the first two principal components (PC), based on genotype data from HapMap CEU, CHB, JPT and YRI population, as well as the stage 1 (genome scan) of the present study.
Figure 5:
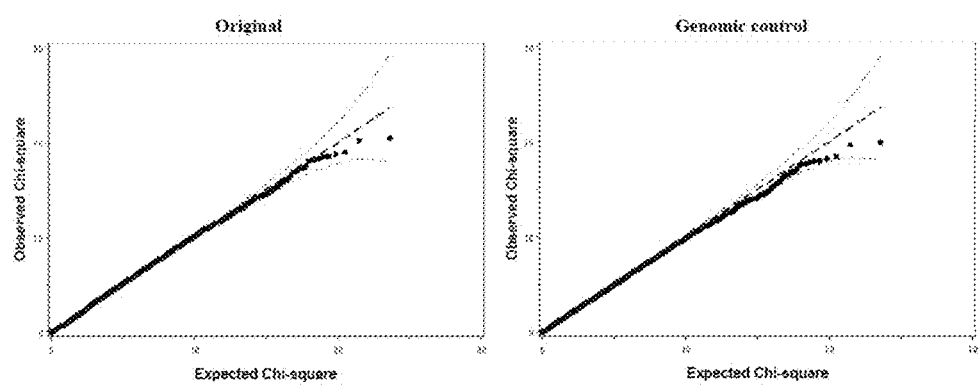
FIG. 5: Q-Q plot for the allelic test. Q-Q plots shows the allelic tests based on 425,513 quality SNPs of the initial analysis of 99 cases and 101 controls. The red lines represent the upper and lower boundaries of the 95% confidence bands.

A two-stage GWAS was then conducted to discover susceptibility genetic loci for familial young-onset T2D subjects with obesity. The study was adequately powered to detect moderate effect size of 2-2.5 for common variants with minor allele frequency of 0.2-0.3 in both the discovery and replication cohorts (FIG. 2). In stage 1, the Illumina HumanHap550-Duo BeadChip was used to perform genome-wide scanning in 200 Hong Kong Chinese subjects (101 controls and 99 T2D patients with age of diagnosis<40 years, body mass index (BMI) ≥27 $kg/m^2$ and at least one affected family member) (Table 1). Out of 541,891 genotyped autosomal SNPs, 425,513 SNPs passed quality control (FIG. 2) and were tested for T2D associations using allelic $\chi^2$ tests. No population stratification between T2D and control subjects was detected using multidimensional scaling analysis (FIGS. 3 and 4). There was no substantial change in the stage 1 GWAS results after adjusting for genomic control with the estimated value of $\lambda$=1.028 in allelic tests (FIG. 5).

Figure 6:
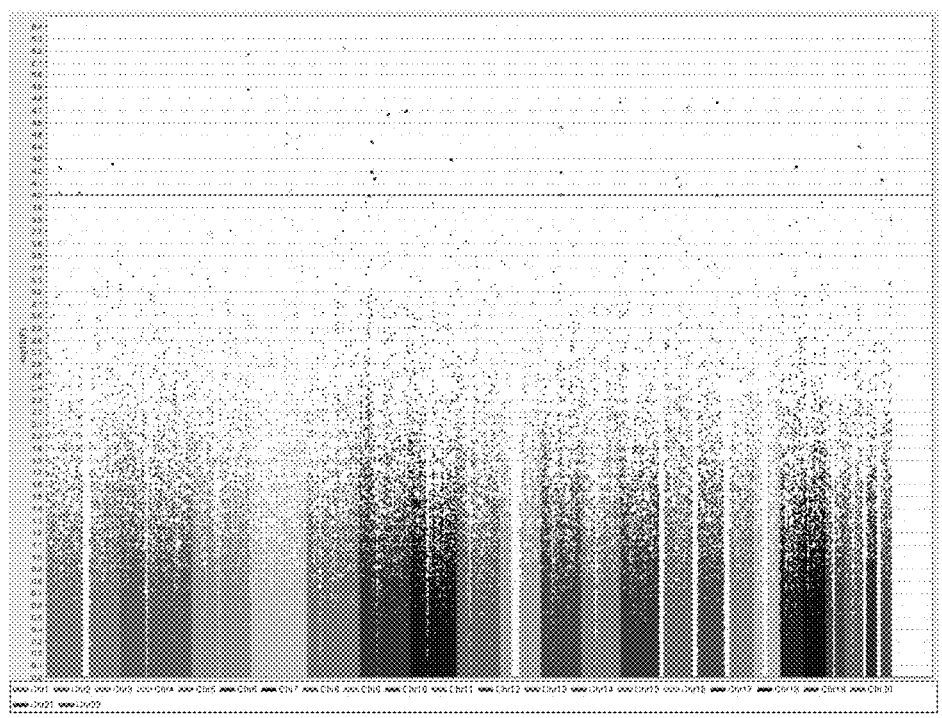
FIG. 6: Association with type 2 diabetes was determined using the allelic model. The y-axis represents the $-\log_{10}$ P value and the x-axis represents the 425,513 analyzed SNPs. The blue line indicates a P value of $1 \times 10^{-4}$.
Figure 7:
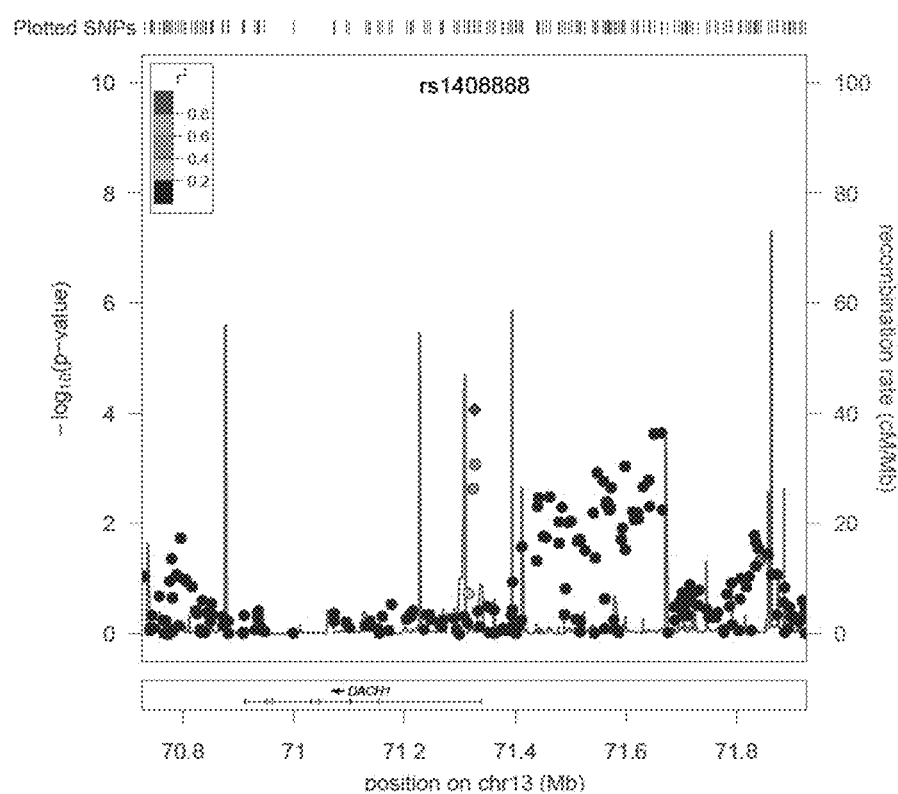
FIG. 7: Regional plot showing significant association of rs1408888 in the DACH1 locus. The $-\log_{10}$ P values for the allelic test from stage 1 (genome scan) were plotted as a function of genomic position (NCBI build 36). Rs1408888 which showed the strongest signal and neighboring genotyped SNPs in the joint analysis were denoted by purple diamond. LD information (based on HapMap) was shown by color-coded points. Two neighboring SNPs rs9572813 and rs17791181, which showed nominal significance and moderate linkage disequilibrium $(0.4 < r^2 < 0.6)$ with rs1408888 were indicated. Estimated recombination rate (the blue line) based on the Japanese and Chinese HapMap population was plotted to reflect the local LD structure around the significant SNPs. Gene annotations were taken from NCBI.

From stage 1 GWAS, 24 unique loci attained an arbitrarily defined significant level of P<$10^{-4}$, which were genotyped in an independent stage 2 cohort (1468 Hong Kong Chinese T2D cases, 1485 healthy controls) for replication (Table S2). Of them, 19 SNPs which passed the quality control criteria were analyzed, and 2 SNPs (rs1408888 and rs1449675) remained significantly associated with T2D (FIGS. 6 and 7). The intronic SNP rs1408888 (stage 1:P=8.4×$10^{-5}$, OR (95% confidence interval, CI)=2.49 (1.57-3.96); stage 2: P=0.0164, OR=1.15 (1.03-1.29)) was located at chromosome 13q21.3 and lies within the gene encoding for DACH1, while the intergenic SNP rs1449675 (stage 1: P=2.0×$10^{-5}$, OR=5.33 (2.30-12.36); stage 2: P=0.0439, OR=1.19 (1.00-1.41)) was located at chromosome 6q25.3. Combining stage 1 and 2 (1567 T2D cases, 1586 controls) for joint analysis revealed three more SNPs (rs6595551 in ZNF608, rs987105 in MUT, and rs1413119 in an intergenic region on chromosome 13) with nominal T2D associations (P<0.05). Among these five SNPs, rs1408888 in DACH1 demonstrated the strongest evidence of association (P=9.1×10$^{-4}$, OR=1.21 (1.08-1.35)). This remained significant (P=0.0176) after using permutation to correct for multiple testings of the 19 SNPs. The risk association of rs1408888 with T2D was then examined in 5 independent Asian case-control cohorts consisting of 7370 cases and 7802 controls (Table S4) with a combined OR of 1.07 (1.02-1.12) (P=0.0112) with no heterogeneity (P=0.107 in Cochran's Q test and 12 (95% CI)=44.8% (0.0%-78.1%) (Table S5). Due to the high frequency of the risk conferring allele (0.72) of rs140888 in the Chinese population, the attributable risk for T2D due to this variant was estimated to range from 0.12 to 0.25 with an OR ranging from 1.10 to 1.22.

Associations with Quantitative Traits in Healthy Adults

The association of metabolic traits with rs1408888 was then examined in healthy adults adjusted for age and gender. The T-allele of DACH1 rs1408888 was associated with increased systolic BP (β(95% CI)=1.56 (1.02-2.10) per T-allele), fasting plasma insulin (β(95% CI)=0.072 (−0.006-0.151) per T-allele) and HOMA-IR (β(95% CI)=0.067 (−0.012-0.145) per T-allele) (Table 2).

Association with Cardiovascular Disease (CVD)

Figure 8:
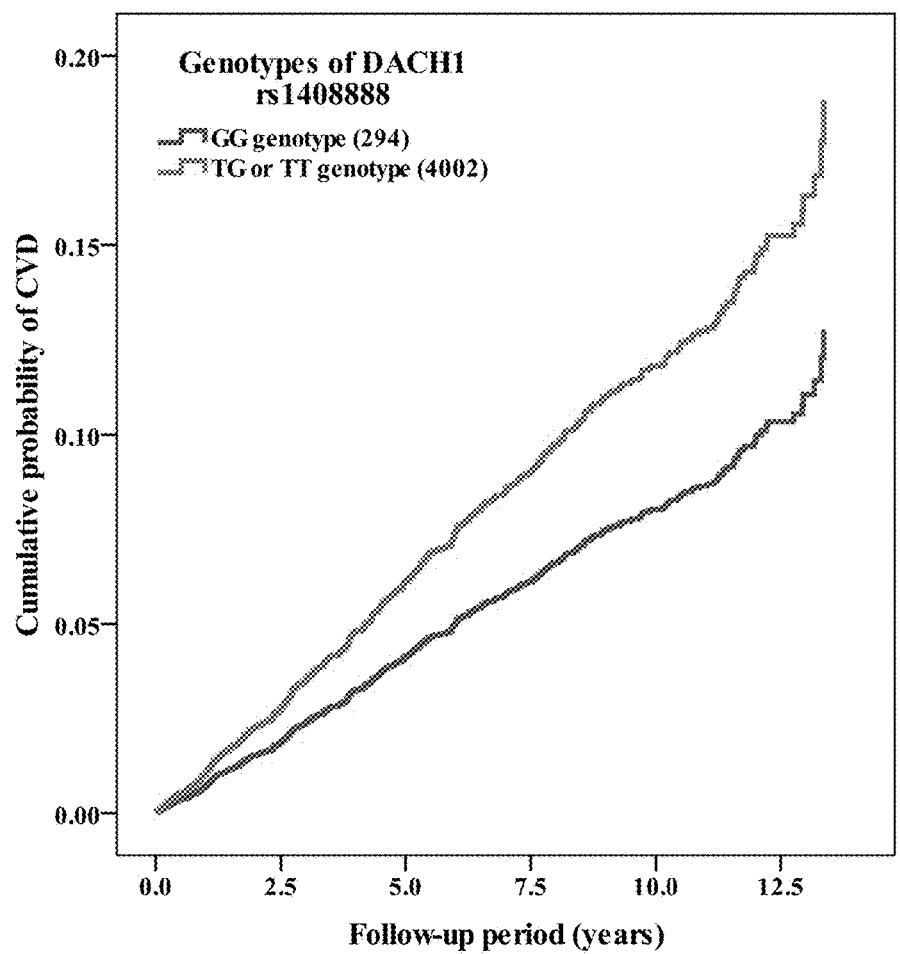
FIG. 8: Kaplan Meier curve showing the cumulative incidence of cardiovascular disease (n=582) in 4296 Chinese type 2 diabetes patients according to their genotype of rs1408888 of DACH1 loci followed up for a mean period of 8.3±3.4 years and after adjustment for conventional risk factors (sex, age and duration of diabetes, use of alcohol and tobacco, waist circumference, $HbA_{1c}$, LDL-cholesterol, HDL-cholesterol, natural logarithm of triglyceride, systolic and diastolic blood pressure, natural logarithms of estimated glomerular filtration rate and urinary albumin:creatinine ratio, retinopathy (present/absent), sensory neuropathy (present/absent) and use of drugs (yes/no)) at baseline. Hazard ratios refer to the risk-conferring allele.

In a separate cohort of 4296 Chinese T2D subjects free of cardiovascular disease at baseline and followed up for 8.3±3.4 years, 582 subjects developed cardiovascular disease. Patients who developed cardiovascular disease had worse cardiometabolic risk and tended to have a higher frequency of T-allele of DACH1 rs1408888 than those without (0.753 versus 0.732, P=0.125) (Table S6). Using the Cox-regression model and after adjustments for risk factors including sex, age, disease duration, tobacco and alcohol intake, waist circumference, glucose and lipid control, estimated glomerular filtration rate (eGFR), albuminuria, retinopathy, sensory neuropathy and use of drugs at baseline (Table S7), the T-allele of DACH1 rs1408888 showed nominal association with cardiovascular disease using the additive genetic model (P=0.1621, HR (95% CI)=1.10 (0.96-1.26)), with significant association in the dominant genetic model (P=0.0451, HR=1.49 (1.01-2.19)). The distribution of GG/GT/TT genotypes were 0.047, 0.400, 0.553 in the cardiovascular disease group and 0.072, 0.392, 0.536 respectively in the group without cardiovascular disease. Using Kaplan Miere analysis, T allele carriers of rs1408888 had higher risk for developing cardiovascular disease than non-carriers (FIG. 8).

Association with Clinicopathological Features in Autopsy Samples

In the autopsy series of 173 non-diabetic cases, DNA was extracted from white blood cells in the spleen to genotype rs1408888 variant which did not depart from Hardy-Weinberg Equilibrium (HWE). Cases with TT genotype were more likely to have a history of coronary heart disease (CHD) (16% versus 6%, P=0.0375) and exhibited pathological features of coronary arteriosclerosis (15% versus 5%, P=0.0287). In a dominant model using GG/GT genotype as referent, TT genotype was associated with an OR 3.27(1.25-11.07, P=0.0184) for coronary arteriosclerosis after adjustment for age, sex and hypertension.

Bioinformatics Analysis

Figure 9:
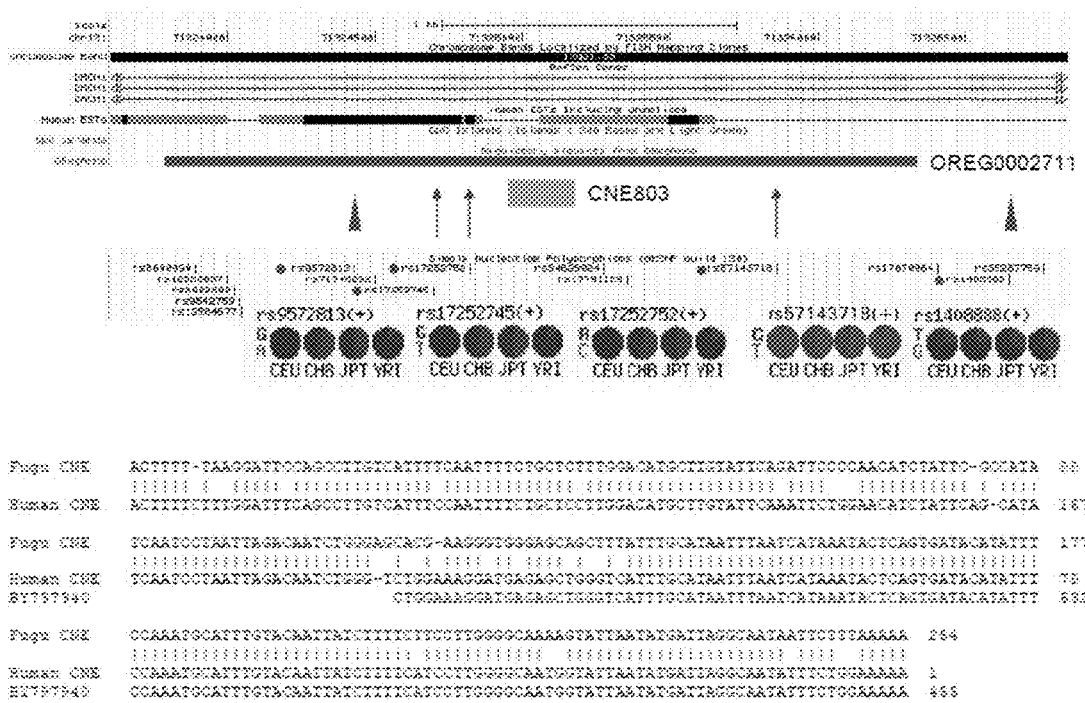
FIG. 9: Bioinformatics analysis of genomic region surrounding rs1408888. The region harboring rs1408888 lies in close vicinity of 2 highly conserved non-coding elements, CNE803 and OREG0002711. The two arrowheads at the end indicate the positions of rs1408888 (right dot) and rs9572813 (left dot). The three internal arrows indicate the positions of the three SNPs (rs17252745, rs17252752 and rs7143718, dots from left to right) genotyped by sequencing. The allele frequencies of the SNPs are shown in pie chart at the bottom. The alignment of the highly conserved Fugu CNE803 (SEQ ID NO:1), the human sequence (SEQ ID NO:2) corresponding to the Fugu CNE and the eye prepared EST BY797940 (SEQ ID NO:3) are also shown.

Two neighboring SNPs in weak LD ($r^2$≈0.5) with rs1408888, rs9572813 and rs17791181, also showed nominal association with T2D (P=0.01-0.001) in the GWAS analysis (FIG. 9). Bioinformatics analysis revealed that the region between rs1408888 and rs9572813 overlapped with a regulatory element conserved from fugu fish to human (Nobrega, *Science*, 2003. 302(5644): p. 413). This element (OREG0002711 from website oreganno.org/oregano/ or chr13:72,425,787-72,428,335 [hg19] from website enhancer.lbl.gov/frnt_page_n.shtml) shows an enhancer activity to direct the distinct expression of a β-galactosidase reporter gene in the eye, cranial nerve, forebrain, hindbrain and neural tube in the mouse embryos (Nobrega 2003 supra; Pennacchio et al., *Nature*, 2006. 444(7118): p. 499-502). In this genomic region, another highly conserved CNE has been reported by an independent group (FIG. 9) (Woolfe et al., *PLoS Biol,* 2005. 3(1): p. e7). This element (CNE803) is conserved in vertebrates and shows homology to an EST from the human eye (BY797940) (FIG. 9), suggesting that this conserved region may be transcribed for a non-coding RNA.

Additional Experiments

The region between rs1408888 and rs9572813 were sequenced in 200 subjects with GWAS data and did not discover novel genetic variants in the CNE803 element nor in the surrounding regions. However, this genomic region contains multiple SNPs, three of them (rs17252745, rs17252752 and rs57143718) showed marked differences in allele frequencies between Asians (CHB and JBT) and Caucasians (CEU) in the NCBI SNP database (FIG. 9) (website ncbi.nlm.nih.gov/snp/). These three SNPs (rs17252745, rs17252752, rs57143718) also showed nominal significance for risk association with T2D, one of which (T allele of rs57143718) was replicated in an expanded case-control cohort of 471 young-onset T2D patients and 280 controls (P=0.036, OR=1.26 (1.02-1.56)).

Figure 10:
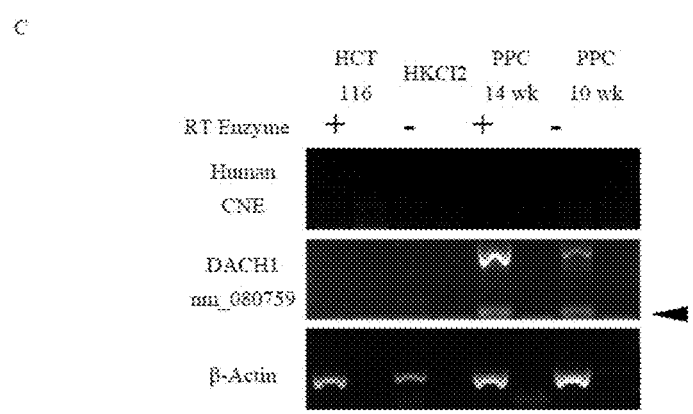
FIG. 10: Expression of the full length DACH1 transcript (nm_080759) in the 10-week and 14-week pancreatic progenitor cells (PPC) were detected by reverse transcription PCR. Primer from an exon expressed only in the full length isoform detected a band with expected size (650 bp) and a smaller novel isoform (arrowhead) in the PPCs. Primers from the highly conserved CNE region did not detect any signal in the PPCs, HCT116 colon cancer cells or HKCl2 hepatocellular carcinoma cells (top panel). Expression of the ubiquitously expressed β-actin was shown in the bottom panel.

Reverse transcription PCR and Northern blot were used to examine the expression of CNE 803 in pancreatic progenitor cells (PPC) (Suen et al., *Int J Biochem Cell Biol,* 2008. 40(4): p. 789-803) and cancer cells which was negative. Expression of multiple DACH1 isoforms was detected in PPC from 10-week and 14-week embryos using reverse transcription PCR (FIG. 10).

Discussion

Using an adequately powered GWAS to detect common SNPs (MAP>0.3) with moderate effect size (OR of 2-2.5) (FIG. 2) applied to a carefully selected case-control cohort of familial young-onset diabetes and obesity, the inventors discovered risk association of T2D with the T allele of rs1408888 of DACH1 with a MAF of 0.75. This was confirmed in other Asian populations with older age and less stringent selection criteria on metaanalysis. Using multiple cohorts, the associations of the risk-conferring T allele with insulin resistance and high blood pressure were also confirmed in normal subjects, incident cardiovascular disease in T2D subjects and pathophysiological evidence of arterial sclerosis in coronary and pancreatic vasculatures in autopsy samples. This is the first study to report an association of DACH1 genetic variants with T2D and cardiovascular disease. Subsequent bioinformatics analysis further supported the clinical relevance of this variant located in a highly conserved region within the intronic region of DACH1, implicated in pancreatic islet development (Kalousova et al., *Dev Biol,* 2010. 348(2): p. 143-52).

Known Function of DACH1

DACH1, located on chromosome 13q21, is the mammalian homologue of the *Drosophila* dachshund (dac) gene which encodes a well-conserved nuclear protein. It is a key component of the retinal determination gene network that governs cell fate and plays a key role in ocular, limb, brain, and gonadal development (Popov et al., *Trends Endocrinol Metab,* 2010. 21(1): p. 41-9). DACH1 knockout mice die shortly after birth, with no gross histological abnormalities with eyes, limbs, or brain, suggesting possible role of DACH1 in perinatal development (Backman et al., *Dev Dyn*, 2003. 226(1): p. 139-44; Davis et al., *Mol Cell Biol*, 2001. 21(5): p. 1484-90; Davis et al., *Mech Dev*, 2001. 102(1-2): p. 169-79). The DACH1 protein is predominantly nuclear, and contains two domains, DachBox-N and DachBox-C, both of which are highly conserved from *Drosophila* to humans, and is capable of binding to naked DNA.

DACH1 and T2D

In the publicly-available genome scans for T2D, the Wellcome Trust Case Control Consortium (Zeggini et al., 2007, supra) and Diabetes Genetics Initiative (Nobrega 2003 supra), DACH1 was among the list of genes that showed nominal association (p<0.05) with T2D (Table S10i) (Dreja et al., *Diabetologia*, 2010. 53(2): p. 309-20). In a mouse model of diet-induced beta cell dysfunction, islet DACH1 gene expression was significantly reduced in prediabetic animals fed a high-fat diet. In both zebra fish and mice, loss of DACH1 resulted in reduced numbers of all islet cell types, including insulin-producing beta-cells (Kalousova et al., 2010 supra). Although deletion of DACH1 in mice did not affect the number of pancreatic progenitor cells, it blocked the perinatal burst of proliferation of differentiated beta-cells (Kalousova et al., 2010 supra). These studies indicate DACH1 as a candidate gene for islet development including perinatal programming.

DACH1 and Intermediate Phenotypes

In the control subjects, the T allele of DACH1 rs1408888 was associated with high BP, insulin resistance and hyperinsulinemia which are well known prediabetic traits (Kahn et al., *Nature*, 2006. 444(7121): p. 840-6). Thus, it is plausible that this variant may be located within or linked to other loci which confer a thrifty phenotype conducive to survival during subsistent lifestyle but increases risk of T2D, obesity and cardiovascular disease in modern societies (Neel, *Am J Hum Genet*, 1962. 14: p. 353-62).

DACH1 and Cardiovascular Disease (CVD)

In a large prospective cohort, the T allele increased risk of CVD by 45% after adjustment for confounders. These findings are consistent with its association with T2D, insulin resistance and high BP in normal subjects as well as that with pathological features of arterial sclerosis in pancreatic and coronary vasculatures and CVD-related death in autopsy cases of non-diabetic subjects. DACH1 is a nuclear protein that binds to DNA or other transcription factors to modulate their activities (Wilson et al., *Structure*, 2004. 12(5): p. 785-92; Wu et al., *Mol Biol Cell*, 2007. 18(3): p. 755-67; Zhou et al., *J Biol Chem*, 2010. 285(51): p. 40342-50; Zhou et al., *Proc Natl Acad Sci USA*, 2010. 107(15): p. 6864-9). Herein, DACH1 can bind to Smad4 and repress TGFβ signaling including TGFβ-induced apoptosis (Wu et al., *J Biol Chem*, 2003. 278(51): p. 51673-84). To this end, the TGFβ signaling pathway is an important pathway in heart and vascular development with increased TGFβ1 activity implicated in hypertension and progressive myocardial fibrosis (Lim and Zhu, *Cell Mol Life Sci*, 2006. 63(22): p. 2584-96; Ramos-Mondragon et al., *Vasc Health Risk Manag*, 2008. 4(6): p. 1289-300; Yang et al., *J Diabetes*, 2010. 2(4): p. 233-42)

DACH1 and Renal Disease

Chronic kidney disease is a well-recognized risk factor for cardiovascular disease in diabetic and non-diabetic population (Go et al., *N Engl J Med*, 2004. 351(13): p. 1296-305; So et al., *Diabetes Care*, 2006. 29(9): p. 2046-52), including Chinese T2D patients. In a recent meta-analysis of GWAS from 20 predominantly population-based studies, DACH1 was discovered as a novel gene region associated with renal function and chronic kidney disease (Kottgen, *Am J Kidney Dis*, 2010. 56(4): p. 743-58). Although the reported SNP is different from rs1408888, the latter is relatively rare in Caucasian populations (Table S10). Although no association between DACH1 genotype and renal function was detected as measured by eGFR in our T2D subjects, this might be due to inter-ethnic differences in allelic distribution, LD block and recombination sites as well as the large number of causal, mediating and modifying factors on intermediate traits and clinical outcomes. To this end, the risk association of T allele with cardiovascular disease in our T2D cohort remained significant after adjustment for conventional risk factors including estimated glomerular filtration rate (eGFR). Given the biological plausibility of the gene function and association of its genetic variants with multiple phenotypes in different cohorts, DACH1 is likely to play an important role in development of insulin resistance, obesity, T2D and cardiovascular-renal complications, at least in Chinese populations.

DACH1 and Cancer

In keeping with its role in cell development, altered expression of DACH1 has been reported in human breast, prostate, ovarian, and endometrial cancers. In these tumors, reduced expression of DACH1 was often linked with poor prognosis (Sunde et al., *Cancer Res*, 2006. 66(17): p. 8404-12; Wu et al., *J Biol Chem*, 2011. 286(3): p. 2132-42; Wu et al., *Proc Natl Acad Sci USA*, 2008. 105(19): p. 6924-9; Wu et al., *Cancer Res*, 2009. 69(8): p. 3347-55). In breast cancer cells, DACH1 binds to Smad4 to inhibit TGF-β signaling and represses TGF-β induced apoptosis (Wu et al., 2003 supra). In 3T3 fibroblast, DACH1 was demonstrated to repress c-jun transcription and bind c-Jun protein to inhibit AP-1 transcription activity. This led to the inhibition of c-Jun-induced DNA synthesis and cellular proliferation (Wu et al., 2007 supra). Recently, DACH1 has been demonstrated to bind to the Forkhead family of transcription factors with reduced forkhead signaling (Zhou et al., *J Biol Chem*, 2010, supra; Zhou et al., *Proc Natl Acad Sci USA*, 2010 supra). These findings strongly suggest that genomic variation of DACH1 or dysregulation of its expression might lead to abnormal cell signaling with major clinical consequences.

Significance of rs1408888

While current body of knowledge supports an important role of DACH1 in islet development, cancer progression and regulation of cardiovascular-renal function, the functional significance of the risk allele of rs1408888 located in the first intron of DACH1 requires further exploration. In the vicinity of rs1408888, conserved elements identified by independent groups (Nobrega, 2003 supra; Pennacchio et al., 2006, supra) can direct a unique gene expression pattern resembling the embryonic expression pattern of DACH1 (Backman et al., 2003, supra; Davis et al., 2001, supra). One of these elements, CNE803 located 1.6 kb upstream from rs1408888, showed sequence homology to an EST from an eye library (BY797940).

The inventors resequenced the region in the original GWAS cohort but did not find any novel SNPs. Three known SNPs, common in Chinese but rare in Caucasians in this region showed associations with T2D in the discovery cohort with one of them being replicated in an expanded case-control cohort of young-onset Chinese T2D patients. Using pancreatic progenitor cells (PPC) and cancer cells, the inventors were unable to detect expression of CNE803 although they found expression of multiple isoforms of DACH1 in the PPC (FIG. 10). Further bioinformatics analysis suggested that rs1408888 was located in a region which may be subject to regulation for genomic expression including chromatin modification in pancreatic islets (Gaulton et al., *Nat Genet.* 42(3): p. 255-9) and through binding with multiple transcription factors, some of which have been implicated in T2D, e.g., hepatic nuclear factor 1 alpha (Table S9).

Conclusion

In this multi-staged experiment (FIG. 11), the present inventors have discovered risk association of an intronic SNP (rs1408888) of DACH1 with T2D, which was confirmed in a multi-ethnic meta-analysis in Asian populations as well as blood pressure, insulin resistance and CVD in Chinese populations. Given the known function of DACH1 on developmental biology as well as the known expression of DACH1 in pancreatic islets and reported risk associations of chronic kidney disease and T2D with DACH1 loci, albeit with different variants in Caucasian populations, these consistent data in Asian populations support an important role of DACH1 loci in the pathogenesis of complex disease including insulin resistance, obesity, T2D and cardiovascular-renal diseases.

Research Design and Methods

Subjects

Hong Kong Chinese Population

The present inventors have previously described the study design, ascertainment, inclusion criteria and phenotyping procedures of subjects included in this study (Ng et al., Diabetes, 2008 supra; Yang et al., *Arch Intern Med,* 2008. 168(5): p. 451-7). All subjects were of southern Han Chinese ancestry residing in Hong Kong. The entire control cohort consisted of 1) 608 hospital staff and volunteers ascertained from a community-based health screening program (mean age: 41.4±0.5 years, 45% male; and 2) 978 adolescents ascertained from a community-based school survey (mean age 15.3±1.9 years, 45% male) with fasting plasma glucose (FPG)<6.1 mmol/l.

Type 2 diabetes was diagnosed according to the 1998 World Health Organization (WHO) criteria. Patients with classical type 1 diabetes with acute ketotic presentation or continuous requirement of insulin within 1 year of diagnosis were excluded. The entire case cohort consisted of 5773 unrelated T2D patients (mean age 56.5±13.5 years, 45% male, mean duration of T2D 7.1±6.7 years) selected from the Hong Kong Diabetes Registry (HKDR). The latter was established as a quality improvement program at the Prince of Wales Hospital with detailed documentation of clinical information including use of medications (Tong et al., *Diabetes Res Clin Pract,* 2008. 82(3): p. 346-52). Also included were 140 unrelated young-onset T2D patients (age 43.0±12.1 years, 41% male) selected from 200 families enrolled in the HKFDS in the case cohort. Written informed consent was obtained from all adult subjects and parents of adolescents while the adolescents gave verbal consent. This study was approved by the Clinical Research Ethics Committee of the Chinese University of Hong Kong.

A two-stage association study was conducted. In the first stage discovery cohort (stage 1), 99 T2D patients and 101 controls were genotyped using genome-scanning 99 T2D cases were selected from two sources. From HKDR, 63 patients were selected with: 1) young-onset diabetes (age-at-diagnosis (AAD)≤40 years); 2) positive family history of diabetes in first-degree relatives; and 3) BMI ≥27 kg/m² and/or waist circumference ≥94 and 90 cm for men and women, respectively. From HKFDS, 36 T2D patients were selected with previously reported linkage signal to T2D, metabolic syndrome (MES) and obesity in their chromosome 1q region (Tam 2010, supra; Ng et al., *Diabetes,* 2004. 53(6): p. 1609-13). 101 controls were selected using the criteria of 1) no known history of T2D or impaired fasting glucose (IFG) or impaired glucose tolerance (IGT) based on 75 gram oral glucose tolerance test (OGTT); 2) without family history of T2D; and 3) with BMI ≤25 kg/m² and waist circumference ≤90 and 80 cm for men and women, respectively.

In the second stage replication cohort (stage 2), stage 1 SNPs were genotyped with suggestive signals in 1468 T2D patients and 1485 healthy controls. The control cohort consisted of 507 adult and 978 adolescent controls. From HKDR, 572 patients were selected with: 1) young-onset diabetes; and 2) positive family history of diabetes in first-degree relatives. Another 792 cases were randomly selected from the same registry irrespective of AAD.

Table S2 summarizes the clinical characteristics of cases and controls in stage 1 and stage 2 experiments. 599 adults with normal glucose tolerance were selected for analysis with quantitative traits (Table 3). From the HKDR, a subset of 4296 diabetic subjects without cardiovascular disease at enrollment was selected for prospective analysis of risk association with cardiovascular disease (Table S6).

Shanghai Chinese Population 1892 unrelated T2D cases were recruited from the in-patient database of Shanghai Diabetes Institute and 1808 unrelated controls from the Shanghai Diabetes Studies recruited from the general population (Hu et al., *Diabetologia,* 2010. 53(2): p. 290-8; Hu et al., *Diabetologia,* 2009. 52(3): p. 451-6; Jia et al., *Diabetologia,* 2007. 50(2): p. 286-92). All T2D cases met the 1999 WHO criteria. Type 1 diabetes and mitochondrial diabetes were excluded by clinical, immunological and genetic criteria. Control subjects were recruited from community-based epidemiological studies of diabetes and related metabolic disorders. Blood samples obtained at 0 and 120 min of OGTT were measured for plasma glucose levels. All controls had: 1) age ≥40 years; 2) normal glucose tolerant (NGT); and 3) without family history of diabetes. The clinical characteristics of the study subjects are summarized in Table S4.

Korean Population

The Korea Seoul National University Hospital (SNUH) case-control population consisted of 761 unrelated T2D patients registered at the Diabetes Clinic of SNUH, and 632 nondiabetic control subjects. T2D was diagnosed using the WHO criteria (Alberti and Zimmet, *Diabet Med,* 1998. 15(7): p. 539-53). Subjects positive for glutamic acid decarboxylase (GAD) antibodies were excluded. Nondiabetic control subjects were selected based on these criteria: 1) ≥60 year-old; 2) no reported history of T2D; 3) negative family history of diabetes in first-degree relatives; 4) FPG<6.1 mmol/1; and 5) glycated hemoglobin (HbA$_{1c}$)<5.8%. The Institutional Review Board of the Clinical Research Institute in SNUH approved the study protocol. Informed consent for genetic analysis was obtained from each subject. The clinical characteristics of the study subjects are summarized in Table S4.

Singapore Chinese and Malay Population

The Singapore case-control study contained subjects from three sources: 1) 1998 Singapore National Health Survey (NHS98); 2) Singapore Malay Eye Study (SiMES); and 3) Singapore Diabetes Cohorts Study (SDCS) (Tan et al., *J Clin Endocrinol Metab,* 2010. 95(1): p. 390-7).

In the NHS98 cohort, subjects with FPG<6.0 mmol/l and 2 hour post-challenge plasma glucose (2HPG) <7.0 mmol/l were defined as normal glucose tolerance (NGT). Subjects with FPG ≥6.0 and <7.0 mmol/l, and 2HPG≥7.0 and <7.8 mmol/l, were defined as having IFG. Subjects with FPG≥7.0 mmol/l, and 2HPG≥7.8 and <11.1 mmol/l, were defined as IGT. A total of 838 IFG/IGT subjects were excluded, leaving 3032 NGT control subjects (2196 Chinese, 472 Malays, and 364 Indians) available for selection.

Subjects from the NHS98 and SDCS cohorts with: 1) a reported history of T2D; 2) FPG ≥7.0 mmol/l; or 3) 2HPG≥11.1 mmol/l were defined as cases. 453 NHS98 case subjects (224 Chinese, 113 Malays, and 116 Indians) and 1703 SDCS cases (1317 Chinese, 256 Malays, and 130 Indians) were available for selection.

In the SiMES cohort, subjects with non-fasting PG<11.1 mmol/l and HbA1c<6.1% (2 SD above the mean for the nondiabetic population) were defined as controls (N=1785). Subjects with a reported history of T2D or non-fasting PG level≥11.1 mmol/l were defined as cases (N=707).

From these three sources, the inventors included 2010 T2D cases and 1945 NGT controls of Chinese ancestry, and 794 T2D cases and 1240 NGT controls of Malaysian ancestry, for analysis. The clinical characteristics of the study subjects are summarized in Table S4.

Japanese Population

A total of 471 unrelated Japanese T2D patients and 582 nondiabetic control subjects were selected from patients attending the outpatient clinic of Wakayama Medical University Hospital. Diabetes was diagnosed by the WHO criteria. Patients positive for GAD antibodies and/or started on insulin therapy within 3 years of diagnosis were excluded. Nondiabetic control subjects were chosen based on the following criteria: age at least 50 years and HbA1c less than 5.6%. The clinical characteristics of the study subjects are summarized in Table S4.

Definitions of Quantitative Traits

All Hong Kong Chinese subjects were examined in the morning after an overnight fast. Clinical measurements including body weight (BW), height (BH) for BMI, waist (WC), hip circumferences (HC), systolic and diastolic BP (SBP and DBP) were documented. Subjects without known history of diabetes were screened using 75 gram OGTT according to the WHO criteria. Both control subjects and newly diagnosed diabetic subjects had measurements of plasma insulin (PI) at 0 and 30 minutes. Homeostasis model assessment of insulin resistance (HOMA-IR) was calculated as (FPI×FPG)÷22.5, and homeostasis model assessment of beta-cell function (HOMA-β) was calculated as fasting PI×20÷(FPG-3.5) (Matthews et al., *Diabetologia*, 1985. 28(7): p. 412-9).

All cases and controls had fasting blood samples collected for DNA extraction and measurements of $HbA_{1c}$, FPG, lipid profiles (total cholesterol (TC), triglycerides (TG), HDL-cholesterol (HDL-C) and LDL-cholesterol (LDL-C). A timed urine collection (4- or 24-hour) was used to measure urinary albumin:creatinine ratio (ACR). Glomerular filtration rate (eGFR) was estimated using the abbreviated formula developed by the Modification of Diet in Renal Disease (MDRD) further adjusted for the Chinese ethnicity: eGFR=186×(SCR×0.011)−1.154×(age)−0.203×(0.742 if female)×(1.233 if Chinese) where SCR is serum creatinine expressed as μmol/l and 1.233 is the adjusting coefficient for Chinese population (Ma et al., *J Am Soc Nephrol*, 2006. 17(10): p. 2937-44). All laboratory assays have been previously reported.

Definitions of Clinical Endpoints

Hypertension was defined as BP≥130/85 mmHg and/or use of anti-hypertensive medications and/or use of of angiotensin-converting enzyme inhibitors (ACEIs) and/or angiotensin receptor blockers (ARBs). Retinopathy was defined by presence of dot and blot hemorrhages, hard exudates, cotton wool spots, neovascularization, laser scars, or a history of vitrectomy. Use of ACEI or ARBs, anti-hypertensive medications (not including ACEI or ARB), lipid-lowering agents (statins and fibrates), oral blood glucose lowering agents and insulin were available in all T2D patients. All clinical endpoints including hospital admissions and mortality were censored on 30th July, 2005, using databases from the Hospital Authority Central Computer System, which records admissions to all public hospitals. These databases, including the Hong Kong Death Registry, were matched by a unique identification number, the Hong Kong Identity Card number compulsory for all Hong Kong residents and used by all government departments and major organizations. Using the International Classification of Diseases (9th Revision code), CVD was defined as 1) fatal or non-fatal coronary heart disease, or 2) all stroke [fatal or nonfatal] (codes 430-438), haemorrhagic stroke (codes 430-432), ischaemic stroke (codes 433-435) or coronary revascularization (codes 36.0-36.1) or 3) peripheral vascular disease (PVD). Coronary heart disease was defined as myocardial infarction (code 410) or ischemic heart disease (code 411-414). Peripheral vascular disease was defined as: 1) diabetes with peripheral circulatory disorders (Code 250.7), or 2) gangrene (Code 785.4), or 3) peripheral angiopathy in diseases classified elsewhere (code 443.81), or 4) peripheral vascular disease, unspecified (443.9) (Diagnosis 1 to 5), or 5) other (peripheral) vascular shunt or bypass (Procedure code: 39.29), or 6) insertion of non-drug-eluting peripheral vessel stent(s) (Procedure code: 39.90).

Sample Checking in Genome Scan

In stage 1, subjects were excluded from further analysis if: 1) duplicate samples exist; 2) gender call from chromosome X was discordant with gender obtained from medical records; 3) genotype call rate yield<98% (Table S11). Possible familial relationship was detected using estimates of identity-by-descent (IBD) derived from pair-wise analyses of 102,919 independent (r2≈0) and quality SNPs. Evidence of population stratification was looked for using multidimensional scaling analysis (FIGS. 3 and 4), and the inflation factor λ for genomic control (FIG. 5).

Genotyping

In the first stage of genome-scan, study subjects including 99 T2D patients and 101 controls were assayed with Illumina HumanHap550-Duo BeadChip at deCODE Genetics. Of the 541,891 genotyped autosomal SNPs, 116,378 (21%) SNPs were excluded based on these criteria: 1) genotype call rate<0.95; or 2) MAF<0.05; or 3) significant departure from HWE in control subjects (P<0.001). Finally, 425,513 SNPs were analyzed (Table S3).

Figure 11:
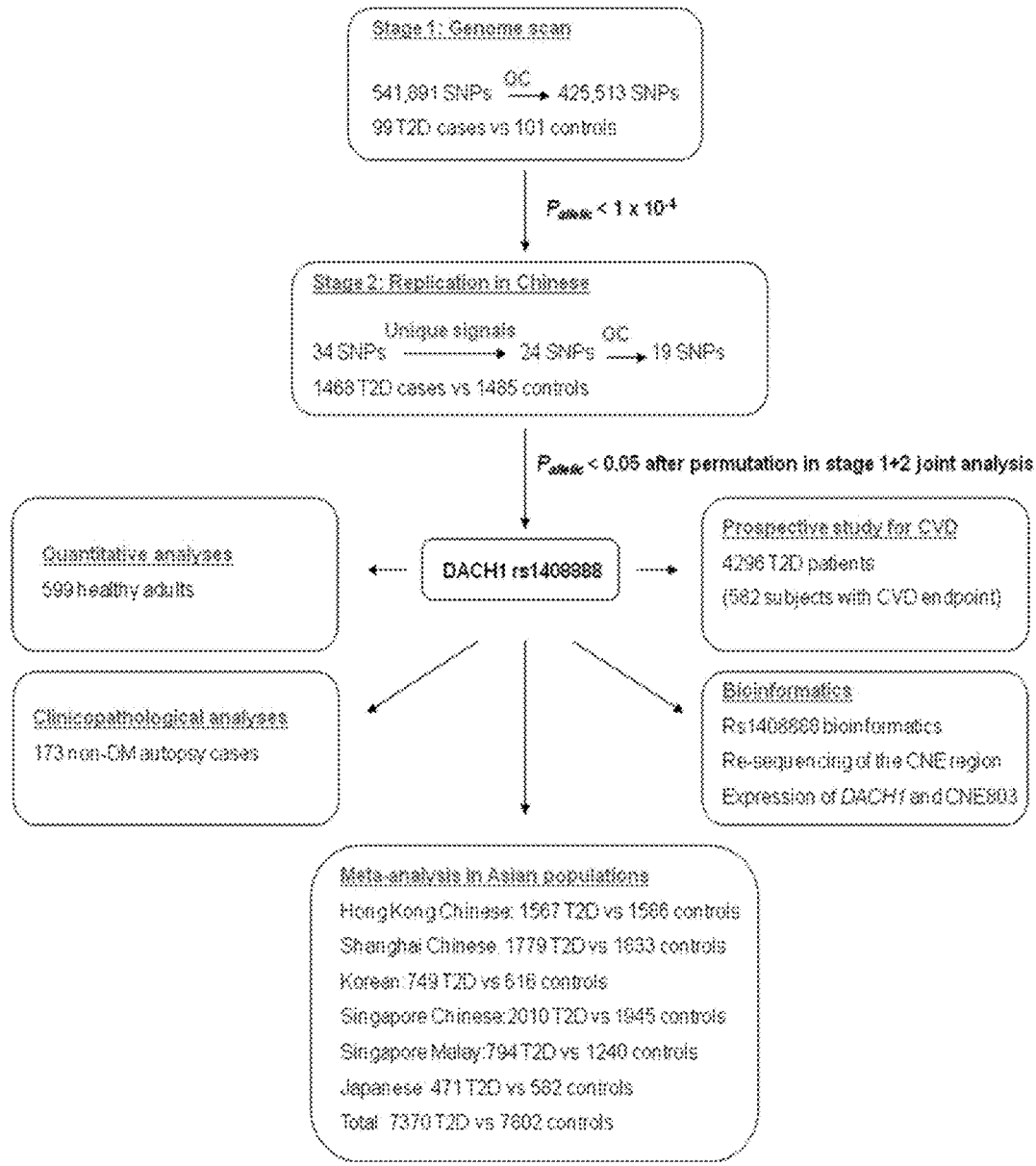
FIG. 11: Flow chart summarizing the study design, subject recruitment, experiments and data analysis.

The study design of the present study was summarized in FIG. 11. In the second stage of replication, 24 qualified SNPs with suggestive association with T2D ($P<1\times10^{-4}$ in allelic test) were further genotyped in an independent case-control cohort (1468 T2D patients, 1485 healthy controls). If a locus had multiple suggestive SNPs in relatively high LD to each other (r2>0.6), only one SNP was genotyped to avoid redundancy. Genotyping was performed at the McGill University and Genome Quebec Innovation Centre using primer extension of multiplex products with detection by MALDI-TOF mass spectroscopy on a Sequenom MassARRAY platform (San Diego, Calif., USA). Out of 24 genotyped SNPs, 5 SNPSs were excluded from analysis due to low call rate (<90%). All 19 remaining SNPs had genotype call rates >90% and were in HWE in control subjects (P>0.05). The genotype concordance rate in 65 blinded duplicate samples was >96%.

For the Shanghai Chinese population, genotyping was performed by primer extension of multiplex products with detection by matrix-assisted laser desorption ionization—time of flight mass spectroscopy using a MassARRAY platform (MassARRAY Compact Analyzer, Sequenom, San Diego, Calif., USA). The call rate and concordance rate of genotypes were 97.5% and 100%, respectively.

For the Korean samples, SNPs were genotyped using Assay-on-Demand TaqMan assays (Applied Biosystems, Foster City, Calif., USA). Allele calling was detected by ABI PRISM 7900HT Sequence Detection System (Applied Biosystems, Foster City, Calif., USA).

For the Singapore study, 2662 and 2031 Chinese subjects were genotyped on the 610Quad and 1Mduov3 platforms, respectively. A total of 3072 Malay subjects were genotyped on the Illumina HumanHap 610Quad. The same procedure of genotype calling used for the Chinese cohort was implemented in the Malays. For each chip in each cohort, a first round of clustering was performed with the proprietary clustering files from Illumina (GenCall). Samples achieving a 99% call rate were subsequently used to generate local clusterfiles (GenTrain) for which a final round of genotype calling was based on. A threshold of 0.15 was implemented on the GenCall score to decide on the confidence of the assigned genotypes. For each chip in individual cohorts, SNPs with call rate <95%, or had gross departure from HWE (P<0.0001), or were monomorphic, were removed.

Statistical Analysis

Statistical analyses were performed using PLINK v1.07 (website: pngu.mgh.harvard.edu/purcell/plink/), SAS v.9.1 (SAS Institute, Cary, N.C., USA) or SPSS for Windows v.15 (SPSS, Chicago, Ill., USA), unless specified otherwise. Haploview v4.1 was used to generate pairwise LD measures and the Manhattan plot for T2D association in the genome-scan. Locus Zoom v1.1 was used to generate the regional plots for T2D associations with significant and previously reported T2D genes. Assuming an additive model with allele frequencies of 0.05-0.30, and an OR of 1.2-3.0 (for a prevalence of 0.1) for T2D risk, the inventors used the Genetic Power Calculator (Purcell et al., *Bioinformatics*, 2003. 19(1): p. 149-50) to estimate the power for stage 1 (genome scan) and stage 2 (replication) at $\alpha$ levels of $1 \times 10^{-4}$ and 0.05, respectively (FIG. 2).

Association with T2D

In the first (genome-scan), second (replication), and joint analysis stages, allelic $\chi^2$ tests in 2×2 contingency tables were used to compare the allele frequencies of autosomal SNPs between T2D cases and healthy controls. Joint analysis was performed by combining the stage 1 and 2 data and expressed as ORs with 95% CI. Multiple testings of SNPs in joint analysis were corrected by permutation for 10,000 times, in which case and control labels were randomly redistributed to subjects. The Quantile-Quantile (Q-Q) plots were used to compare the observed and expected distributions for the 1df $\chi^2$ statistics generated from allelic tests with or without correction for genomic control (GC) in the genome scan stage (FIG. 5).

MIX v1.7 (Bax et al., *BMC Med Res Methodol*, 2006. 6: p. 50) was used to perform meta-analysis, in which combined estimates of the ORs (95% CIs) from multiple case-control groups were calculated by weighting the natural log-transformed ORs (with respect to the same allele) of each study using the inverse of their variance under the fixed effect model. Cochran's Q statistic (P<0.05) and I 2 were used to assess heterogeneity of ORs between studies.

Genomic Control

Genomic control (Devlin and Roeder, *Biometrics*, 1999. 55(4): p. 997-1004) was applied to correct for relatedness of the subjects and adjust for potential population stratification. The inflation factor $\lambda$ was estimated by taking the median of the distribution of the $\chi^2$ statistic from 425,513 quality SNPs in allelic test, and then divided by the median of the expected $\chi^2$ distribution. The inventors calculated the P values corrected for genomic control by dividing the observed $\chi^2$ statistic by $\lambda$.

Quantitative Traits Analyses

All data were presented as mean±SD or median (inter-quartile range), as appropriate. FPI, HOMA-IR and HOMA-β were logarithmically transformed due to skewed distributions. Associations between genotypes and phenotypic traits were tested by multivariate linear regression adjusted for sex and age under the additive genetic model.

Prospective Study for CVD in T2D Subjects

All data were expressed as percentage, mean±SD or median (inter-quartile range), as appropriate. Triglyceride, albumin-to-creatinine ratio (ACR) and eGFR were natural log-transformed due to skewed distributions. Between-group comparisons were performed by chi-squared test for categorical variables, and unpaired Student's t-test or Wilcoxon Rank Sum test for continuous variables.

The relationship between SNPs and outcome variables under additive, dominant and recessive genetic models were tested by Cox proportional hazard regression model, with adjustment for conventional risk factors at baseline including sex, age, duration of diabetes, use of alcohol and tobacco, waist circumference, $HbA_{1c}$, LDL-cholesterol, HDL-cholesterol, natural logarithm of triglyceride, SBP, DBP, natural logarithm of eGFR, natural logarithm of ACR, retinopathy (present/absent), sensory neuropathy (present/absent), use of drugs (yes/no) in 4296 T2D patients without history of CVD at enrollment. Hazard ratios (HRs) with 95% CI were presented.

Association with Pathological Features with DACH1 Genotype in Autopsy Studies

Details of the autopsy specimens and clinical data have been described (Guan et al., *Nephrol Dial Transplant,* 2009. 24(6): p. 1889-95; Zhao et al., *Diabetes,* 2004. 53(11): p. 2984-91). Briefly, consecutive autopsy cases in the Prince of Wales Hospital were included if they had 1) clinical data on hypertension, PG or diabetic status, and 2) a full autopsy report on causes of death. Specimens of pancreas, kidneys and spleen were taken at post-mortem examination, fixed in 10% buffered formalin, and embedded in paraffin blocks. Clinical conditions and parameters including history of cardiovascular disease, BP, PG and renal function taken during clinically stable condition at least 1 month before death were retrieved from hospital records and autopsy reports. DNA was obtained from archived paraffin blocks using white blood cell-concentrated spleen tissues, using a modified DNA-extraction protocol (Guan et al., 2009, supra). Genotyping for rs1408888 was performed using a Taqman genotyping kit from ABI and an ABI 7900HT Fast Real-Time PCR System. Observed distributions of genotypes were analyzed for deviation from HWE by Chi-square tests with one degree of freedom. Categorical variables were compared using Chi-square test or Fisher's exact test. The OR and corresponding 95% CI were calculated using logistic regression. A two-tailed P-value <0.05 was considered significant. Calculations were performed using SPSS (Statistics Package for the Social Sciences 10.0.7 for Windows, 2000, SPSS Inc., Chicago, Ill., USA).

Re-Sequencing of the rs1408888 Genomic Region

The genomic region between rs1408888 and rs9572813 was PCR amplified in 2 DNA fragments for capillary sequencing. The fragment close to rs1408888 was amplified by DACH1-F (5'-TCTTGCTATAAAATGCAT-GAAAGGAG-3'; SEQ ID NO:4) and 1R (5'-ATAGC-CAAAGGGAGGGAAAA-3'; SEQ ID NO:5). The 1.7 Kb DNA fragment was sequenced by 3 primers: 1F (5'-AAGGGCCCATGACAGGAATG-3'; SEQ ID NO:6) and 3F (5'-TCACTCAAGATGAGTTCACACCA-3'; SEQ ID NO:7) in one orientation and 2R (5'-GTTATTATCGGC-CCAATTCC-3'; SEQ ID NO:8) in the opposite orientation. The primer 1F covers the SNP rs57143718 and the primer 3F covers the CNE803 element. The fragment close to rs9572813 was amplified using CNE803-1F (5'-TAATAC-CATTGCCCCAAGGA-3'; SEQ ID NO:9) and DACH1-R (5'-CAGCAAATCCCAGCGTAGCAC-3'; SEQ ID NO:10) as primers. The fragment was sequenced using CNE803-2F (5'-TGACCCAGCTCTCATCCTTT-3'; SEQ ID NO:11) as primer to cover the two SNPs rs17252745 and rs17252752.
Expression of DACH1 and CNEs Detected by Reverse-Transcription PCR Total RNA were prepared from pancreatic progenitor cells (PPC) and cultured cancer cell lines using the TRIzol method. The RNA samples were treated by DNase I to remove contamination of genomic DNA. The first strand cDNA was synthesized by the SuperScript First Strand Synthesis System from Invitrogen. Expression of the CNE was detected by 43 cycles of PCR using 5'-TAATACCAT-TGCCCCAAGGA-3' (SEQ ID NO:12) and 5'-TTTG-GATTTCAGCCTTGTCA-3' (SEQ ID NO:13) as primers. Expression of DACH1 was detected by 40 cycles of PCR using 5'-CTGCACCAACGCAAGTTCTA-3' (SEQ ID NO:14) and 5'-ATAAGCCCATCAGCATCTGG-3' (SEQ ID NO:15) as primers. Expression of β-actin was used as a positive control by 35 PCR cycles using 5'-AGAGCTAC-GAGCTGCCTGAC-3' (SEQ ID NO:16) and 5'-AGCACT-GTGTTGGCGTACAG-3' (SEQ ID NO:17) as primers.

All patents, patent applications, and other publications, including GenBank Accession Numbers, cited in this application are incorporated by reference in the entirety for all purposes.

TABLE 1

Association of SNPs with familial young-onset Type 2 diabetes and obesity in Hong Kong Chinese in a genome-wide association study using Illumina HumanHap550 chip with p values less than $10^{-4}$.

| SNP | Chr. | Nearest gene(s) | Risk allele | Stage | RAF (T2D) | RAF (Controls) | OR (95% CI) | $P_{Allele}$ | Joint analysis of stage 1 + 2 Combined OR (95% CI) | $P_{Allele}$ | $P_{permutation}$ |
|---|---|---|---|---|---|---|---|---|---|---|---|
| rs841859 | 1 | SLC2A1 | G | 1 | 0.237 | 0.089 | 3.18 (1.77-5.71) | $5.8 \times 10^{-5}$ | 1.12 (0.97-1.29) | 0.1386 | 0.9422 |
|  |  |  |  | 2 | 0.134 | 0.131 | 1.03 (0.89-1.2) | 0.6868 |  |  |  |
| rs6661853 | 1 | CNIH3 | G | 1 | 0.798 | 0.614 | 2.48 (1.59-3.89) | $5.4 \times 10^{-5}$ | 0.97 (0.87-1.09) | 0.6128 | 1.0000 |
|  |  |  |  | 2 | 0.714 | 0.733 | 0.91 (0.81-1.02) | 0.1105 |  |  |  |
| rs16862964 | 3 | LPP | G | 1 | 0.480 | 0.262 | 2.59 (1.71-3.94) | $6.7 \times 10^{-6}$ | 0.97 (0.88-1.08) | 0.5845 | 1.0000 |
|  |  |  |  | 2 | 0.347 | 0.369 | 0.91 (0.82-1.01) | 0.0796 |  |  |  |
| rs4834621 | 4 |  | G | 1 | 0.293 | 0.124 | 2.93 (1.75-4.93) | $3.0 \times 10^{-5}$ | 0.97 (0.86-1.09) | 0.6395 | 1.0000 |
|  |  |  |  | 2 | 0.216 | 0.233 | 0.91 (0.8-1.03) | 0.1238 |  |  |  |
| rs7665789 | 4 |  | A | 1 | 0.894 | 0.743 | 2.92 (1.68-5.07) | $8.9 \times 10^{-5}$ | 0.99 (0.86-1.13) | 0.8508 | 1.0000 |
|  |  |  |  | 2 | 0.171 | 0.158 | 0.91 (0.79-1.05) | 0.1975 |  |  |  |
| rs6595551 | 5 | ZNF608 | G | 1 | 0.748 | 0.530 | 2.63 (1.72-4.01) | $5.9 \times 10^{-6}$ | 1.12 (1.01-1.24) | 0.0337 | 0.4836 |
|  |  |  |  | 2 | 0.661 | 0.648 | 1.06 (0.95-1.18) | 0.3159 |  |  |  |
| rs3130932 | 6 | POU5F1 | C | 1 | 0.460 | 0.272 | 2.27 (1.5-3.45) | $1.0 \times 10^{-4}$ | 1.05 (0.94-1.16) | 0.3990 | 0.9999 |
|  |  |  |  | 2 | 0.370 | 0.372 | 0.99 (0.89-1.1) | 0.8889 |  |  |  |
| rs846514 | 6 | LRFN2 | A | 1 | 0.849 | 0.678 | 2.66 (1.63-4.33) | $6.3 \times 10^{-5}$ | 1.04 (0.93-1.17) | 0.4618 | 0.9999 |
|  |  |  |  | 2 | 0.736 | 0.739 | 0.99 (0.88-1.11) | 0.8048 |  |  |  |
| rs987105 | 6 | MUT | G | 1 | 0.939 | 0.807 | 3.71 (1.88-7.32) | $7.1 \times 10^{-5}$ | 1.25 (1.06-1.47) | 0.0875 | 0.1388 |
|  |  |  |  | 2 | 0.101 | 0.115 | 1.15 (0.97-1.37) | 0.0983 |  |  |  |
| rs1325076 | 6 | FUT9 | G | 1 | 0.444 | 0.243 | 2.5 (1.63-3.83) | $2.1 \times 10^{-5}$ | 1.02 (0.92-1.14) | 0.7021 | 1.0000 |
|  |  |  |  | 2 | 0.314 | 0.323 | 0.96 (0.86-1.07) | 0.4651 |  |  |  |
| rs1449675 | 6 |  | A | 1 | 0.965 | 0.837 | 5.33 (2.3-12.36) | $2.0 \times 10^{-5}$ | 1.29 (1.09-1.52) | 0.0025 | 0.0503 |
|  |  |  |  | 2 | 0.098 | 0.115 | 1.19 (1-1.41) | 0.0439 |  |  |  |
| rs10762033 | 10 | CTNNA3 | G | 1 | 0.566 | 0.366 | 2.25 (1.51-3.36) | $6.4 \times 10^{-5}$ | 1.07 (0.97-1.18) | 0.2078 | 0.9897 |
|  |  |  |  | 2 | 0.470 | 0.466 | 1.01 (0.91-1.12) | 0.7964 |  |  |  |
| rs4245124 | 11 | SPATA19 | C | 1 | 0.697 | 0.485 | 2.44 (1.62-3.68) | $1.7 \times 10^{-5}$ | 1.07 (0.96-1.18) | 0.2213 | 0.9922 |
|  |  |  |  | 2 | 0.380 | 0.382 | 1.01 (0.9-1.12) | 0.9090 |  |  |  |

*Nearest Entrez genes within 250 kb

Stage 1 (genome scan) included 99 young-onset familial T2D patients and 101 controls.

Stage 2 (replication stage) included 1468 T2D patients and 1485 controls.

$P_{Allele}$ and $P_{permutation}$ represent P values of allelic test and after permutation of 10,000 times based on 19 SNPs in stage 2, respectively.

Risk allele refers to the allele with a higher frequency in T2D patients than in controls in stage 1.

RAF (T2D) and RAF (Controls), risk allele frequencies in T2D patients and controls, respectively.

OR, odds ratio are reported with respect to the risk allele.

TABLE 2

Clinical and metabolic characteristics of healthy adults stratified according to the genotypes of DACH1 rs1408888.

| Characteristics | Hong Kong Adults | | | |
|---|---|---|---|---|
| | GG (N = 55) | GT (N = 246) | TT (N = 298) | P |
| Body mass index (kg/m$^2$) | 22.7 ± 3.8 | 22.9 ± 3.3 | 23.0 ± 3.3 | 0.801 |
| Waist circumference (cm) | 74.7 ± 10.7 | 76.7 ± 9.8 | 77.2 ± 9.1 | 0.780 |
| Hip circumference (cm) | 92.8 ± 6.4 | 93.3 ± 6.3 | 93.6 ± 5.8 | 0.624 |
| Systolic BP (mmHg) | 111 ± 14.5 | 114.3 ± 16.1 | 116.8 ± 16.9 | 0.030 |
| Diastolic BP (mmHg) | 68.6 ± 10.8 | 72.2 ± 11 | 72.9 ± 11.5 | 0.073 |
| Total cholesterol (mmol/l) | 4.7 ± 0.8 | 5 ± 0.9 | 5.1 ± 1 | 0.025 |
| Triglyceride (mmol/l) | 0.7 (0.6-1.1) | 0.9 (0.6-1.3) | 0.9 (0.7-1.3) | 0.547 |
| HDL-C (mmol/l) | 1.5 ± 0.4 | 1.6 ± 0.4 | 1.5 ± 0.4 | 0.306 |
| LDL-C (mmol/l) | 2.8 ± 0.8 | 3 ± 0.8 | 3 ± 0.9 | 0.071 |
| Fasting plasma glucose (mmol/l) | 4.9 (4.5-5.2) | 4.8 (4.6-5.1) | 4.8 (4.6-5.1) | 0.709 |
| Fasting plasma insulin (pmol/l) | 39.9 (23.1-51.2) | 40.2 (24.4-55.9) | 42.4 (29.7-61.6) | 0.014 |
| HOMA of insulin resistance | 1.4 (0.8-1.9) | 1.5 (0.9-2.0) | 1.5 (1-2.2) | 0.019 |
| HOMA of beta cell function | 93.6 (68.1-135.6) | 99 (63.4-162.6) | 112.5 (71.0-167.6) | 0.010 |
| Insulinogenic index (mU/mmol): | 13.9 (8.1-21.4) | 15.5 (9.3-23.6) | 16.3 (9.7-25.6) | 0.2369 |
| Beta cell function (×10$^{-6}$): | 26.6 (19.4-35.2) | 28.3 (18.6-38.7) | 32.1 (21-44.2) | 0.0804 |

Data are expressed as n, mean ± SD or median (interquartile range). P values were calculated from linear regression adjusted for sex and age assuming an additive model. (please formula for all 4 indexes HOMA-IR, HOMA-B, ID, ??disposal index)

TABLE 3

Clinicopathological characteristics associated with rs1408888 genotype of DACH1 in autopsy series of Chinese non-diabetic subjects.

| | TT N = 90 | TG/GG N = 83 | P value (TT vs TG/GG) |
|---|---|---|---|
| Age(year) | 67.0 ± 15.7 | 70.6 ± 15.7 | 0.1277 |
| Female | 42.2 (38) | 51.8 (43) | 0.2069 |
| Clinical details | | | |
| Hypertension | 14.4 (13) | 14.5 (12) | 0.9980 |
| Coronary heart disease (CHD) | 17.8 (16) | 7.2 (6) | 0.0375 |
| Stroke | 10.0 (9) | 8.4 (7) | 0.7224 |
| End stage renal disease | 3.3 (3) | 7.2 (6) | 0.3147 |
| Death due to cardiovascular disease | 20.0 (18) | 12.0 (10) | 0.1560 |
| Death due to renal disease | 1.1 (1) | 0.0 (0) | 1.0000 |
| Vascular lesions | | | |
| Coronary arterial sclerosis | 16.7 (15) | 6.0 (5) | 0.0287 |
| Left ventricular hypertrophy | 3.3 (3) | 4.8 (4) | 0.7115 |
| Pancreas lesions | | | |
| Vascular lesions | 16.7 (15) | 27.7 (23) | 0.0796 |
| Arteriosclerosis | 15.6 (14) | 22.9 (19) | 0.2198 |
| Hyaline arteriolosclerosis | 6.7 (6) | 9.6 (8) | 0.4740 |
| Interstitial lesions | 64.4 (58) | 54.2 (45) | 0.1709 |
| Interstitial fibrosis | 24.4 (22) | 15.7 (13) | 0.1509 |
| Interstitial fat infiltration | 53.3 (48) | 50.6 (42) | 0.7194 |
| Islet amyloidosis | 2.2 (2) | 2.4 (2) | 1.0000 |
| Vascular interstitial lesions | 68.9 (62) | 66.3 (55) | 0.7125 |
| Near normal structure | 24.4 (22) | 25.3 (21) | 0.8964 |
| Renal pathology | | | |
| Glomerular lesion | 51.1 (46) | 54.2 (45) | 0.6827 |
| Global glomeruler sclerosis | 43.3 (39) | 49.4 (41) | 0.4242 |
| Glomerular hypertrophy | 10.0 (9) | 16.9 (14) | 0.1838 |
| Vascular lesions | 56.7 (51) | 61.4 (51) | 0.5232 |
| Hyaline arteriolosclerosis | 8.9 (8) | 10.8 (9) | 0.6661 |
| Arteriosclerosis | 55.6 (50) | 61.4 (51) | 0.4323 |
| Tubulointerstitial lesions | 47.8 (43) | 47.0 (39) | 0.9172 |
| Tubular lesion | 25.6 (23) | 31.3 (26) | 0.4001 |
| Interstitial fibrosis | 41.1 (37) | 37.3 (31) | 0.6128 |
| Vascular-tubulointerstitial lesions | 66.7 (60) | 68.7 (57) | 0.7779 |
| Near normal structure | 26.7 (24) | 25.3 (21) | 0.8379 |

Data are shown as mean ± SD or % (N) and were compared by the Student t-test, chi-square test or Fisher's exact test.

TABLE S1

In silico replication of previously reported loci and SNPs associated with T2D.

| Genes | Chr | SNPs | B36 Position (sp) | Previous GWAS | | | | |
|---|---|---|---|---|---|---|---|---|
| | | | | T2D Risk/ non-risk allele | Control frequency for risk allele (Hapmap CEU) | OR | N (case/control) | References for OR |
| IGF2BF2 | 3 | rs1881282 | 12365125 | C/G | 0.903 | 1.14 (1.03-1.26) | 14586/17968 | [1] |
| KCNJ11 | 11 | rs5219 (r$^2$ = 0.9) | 17366148 | C/T | 0.398 | 1.14 (1.10-1.19) | 14586/17968 | [1] |
| CDKAL1 | 6 | rs7756992a | 20787688 | G/A | 0.279 | 1.26 (1.18-1.34) | 4549/5579 | [2] |
| CDKN2A/B | 9 | rs10811661 (r$^3$ = 0.98) | 22124094 | T/C | 0.801 | 1.20 (1.14-1.25) | 14586/17968 | [1] |
| HHEX | 10 | rs1111875a | 94452862 | C/T | 0.584 | 1.13 (1.09-1.17) | 14586/17968 | [1] |
| IGF1BP2 | 3 | rs4402960a | 186994381 | T/G | 0.296 | 1.14 (1.11-1.18) | 14586/17968 | [1] |
| SLC30A8 | 8 | rs13266634a | 118253964 | C/T | 0.761 | 1.12 (1.07-1.16) | 14586/17968 | [1] |
| FTO | 16 | rs8050136a | 52373776 | A/C | 0.46 | 1.17 (1.12-1.23) | 14586/17968 | [1] |

TABLE S1-continued

In silico replication of previously reported loci and SNPs associated with T2D.

| | | | | | | | | |
|---|---|---|---|---|---|---|---|---|
| TCF7L3 | 10 | rs7903146 | 114748339 | T/C | 0.279 | 1.37 (1.31-1.43) | 14586/17968 | [1] |
| JAZF1 | 7 | rs864745 ($r^2$ = 0.97) | 27953796 | T/C | 0.487 | 1.10 (1.07-1.33) | 28645/39397 | [2] |
| CDC123, CAMK1D | 10 | rs12779790 | 12368016 | G/A | 0.229 | 1.11 (1.07-1.14) | 28645/39397 | [2] |
| ISPAN8, LGR5 | 12 | rs7951581 ($r^2$ = 1) | 69949369 | C/T | 0.252 | 1.09 (1.06-1.12) | 28645/39397 | [2] |
| THADA | 2 | rs7578597 | 43586327 | T/C | 0.876 | 1.95 (1.03-3.67) | 28645/39397 | [2] |
| ADAMTS9 | 3 | rs4607103 ($r^2$ = 0.89) | 64586944 | C/T | 0.81 | 1.09 (1.06-1.12) | 28645/39397 | [2] |
| NOTCH2 | 1 | rs10923931 | 120319482 | T/G | 0.093 | 1.13 (1.08-1.17) | 28645/39397 | [2] |
| MTNR1B | 11 | rs1387153a | 92313476 | T/C | 0.272 | 1.09 (1.05-1.12) | 40655/67022 | [3] |
| TCF2(HNF1B) | 17 | rs4430796a | 33172153 | G/A | 0.509 | 1.10 (1.06-1.15) | 9936/23087 | [4] |
| WFS1 | 4 | rs734312a | 6354255 | A/G | 0.65 | 1.09 (1.05-1.14) | 9533/11389 | [5] |

| | Present study (stage 3) | | | |
|---|---|---|---|---|
| Genes | T2D Risk/nonrisk allele | Control frequency for risk allele (HK GWAS) | OR | P value |
| IGF2BF2 | — | — | — | — |
| KCNJ11 | C/T | 0.3119 | 1.13 (0.74-1.72) | 0.5715 |
| CDKAL1 | G/A | 0.401 | 1.46 (0.99-2.18) | 0.0588 |
| CDKN2A/B | T/C | 0.515 | 2.02 (1.35-3.03) | 0.0007 |
| HHEX | C/T | 0.2673 | 1.25 (0.81-1.93) | 0.3128 |
| IGF1BP2 | T/G | 0.2475 | 1.14 (0.73-1.78) | 0.5656 |
| SLC30A8 | T/C | 0.5149 | 1.47 (1.00-2.22) | 0.0523 |
| FTO | A/C | 0.09406 | 2.59 (1.45-4.64) | 0.0010 |
| TCF7L2 | — | — | — | — |
| JAZF1 | C/T | 0.1832 | 1.55 (0.96-2.50) | 0.0725 |
| CDC123, CAMK1D | — | — | — | — |
| ISPAN8, LGR5 | T/C | 0.7921 | 1.25 (0.76-2.08) | 0.3820 |
| THADA | — | — | — | — |
| ADAMTS9 | C/T | 0.6634 | 1.20 (0.78-1.82) | 0.4064 |
| NOTCH2 | — | — | — | — |
| MTNR1B | C/T | 0.5198 | 1.02 (0.68-1.52) | 0.9131 |
| TCF2(HNF1B) | G/A | 0.2228 | 1.25 (0.78-1.99) | 0.3503 |
| WFS1 | G/A | 0.2079 | 1.03 (0.63-1.66) | 0.9179 | a Reported SNPs associated with T2D in previous GWA scans and genotyped in our GWA scan.

References:

[1] Zeggini, E., et al., Science, (2007) 316: 1336-41;

[2] Zeggini. E., et al., Nat Genet, (2008) 40: 638-45;

[3] Dupuis, J., et al., Nat Genet, 42: 105-16;

[4] Gudmundsson, J., et al., Nat Genet., (2007) 39: 977-83;

[5] Sandhu, M. S., et al., Nat Genet(2007) 39: 951-3.

TABLE S2

Clinical characteristics of subjects in stage 1 and 2 experiments.

| | Stage 1 (genome scan) | | Stage 2 (replication) | | |
|---|---|---|---|---|---|
| Characteristics | T2D Patients | Controls | T2D Patients | Healthy Adults | Healthy Adolescents |
| N (male/female) | 99 (40/59) | 101 (37/64) | 1468 (592/876) | 507 (234/273) | 978 (457/521) |
| Age (years) | 40.6 ± 8.8 | 37.4 ± 10.1 | 50 ± 13.8 | 42.2 ± 10.4 | 15.3 ± 1.9 |
| Age-at-diagnosis (year) | 31.8 ± 7.7 | — | 44.0 ± 13.6 | — | — |
| Disease duration (years) | 8.0 ± 8.3 | — | 6.0 ± 6.4 | — | — |
| Body mass index (kg/m$^2$) | 30.9 ± 4.4 | 20.8 ± 2 | 24.8 ± 3.9 | 23.3 ± 3.4 | 19.9 ± 3.6 |
| HbA$_{1C}$ (%) | 8.0 ± 1.9 | — | 8.0 ± 2.0 | — | — |
| Fasting plasma glucose (mmol/l) | — | 4.7 ± 0.4 | — | 4.9 ± 0.4 | 4.7 ± 0.3 |

Data are shown as N, mean ± SD or median (interquartile range).

TABLE S3

Quality control of genotyping results

| | Stage 1 (Genome scan) | Stage 2 (Replication) |
|---|---|---|
| Number of SNPs before QC in chromosome 1-22 | 541.891 | 24 |
| Exclusion criteria: | | |
| SNPs with overall call rate <0.95 (or <0.90) | 2.311 | 5 |
| SNPs with overall MAF <0.05 | 113.596 | 0 |
| SNPs with HWE for control ($P < 10^{-3}$) | 947 | 0 |
| Number of SNPs after QC in chromosome 1-22 | 425.513 | 19 |

TABLE S4

Clinical characteristics of subjects in other Asian populations.

| | Shanghai Chinese | | Japanese | | Korean | |
|---|---|---|---|---|---|---|
| Characteristics | T2D Patients | Controls | T2D Patients | Controls | T2D Patients | Controls |
| n | 1892 | 1808 | 471 | 582 | 761 | 632 |
| (male/female) | (988/904) | (748/1059) | (262/209) | (204/378) | (354/407) | (286/346) |
| Age (years) | 61.2 ± 12.6 | 57.3 ± 12.3 | 61.6 ± 10.4 | 67.9 ± 9.1 | 59.2 ± 9.9 | 64.7 ± 3.6 |
| Age-at-diagnosis (year) | 54.1 ± 11.8 | — | 46.2 ± 8.0 | — | 50.0 ± 10.3 | — |
| Disease duration (years) | 6.0 (1.0-10.0) | — | 15.4 ± 9.5 | — | 9.2 ± 7.8 | — |
| Body mass index (kg/m$^2$) | 24.1 ± 3.5 | 23.6 ± 4.2 | 24.2 ± 3.8 | 22.4 ± 3.2 | 24.5 ± 2.9 | 23.5 ± 3.1 |
| HbA$_{IC}$ (%) | 9.2 ± 2.4 | — | 7.9 ± 1.6 | 5.0 ± 0.4 | 8.1 ± 1.6 | 5.3 ± 0.3 |
| Fasting plasma glucose (mmol/l) | 13.0 ± 5.2 | 5.0 ± 0.5 | — | — | 8.6 ± 2.6 | 5.0 ± 0.5 |

| | Singapore Chinese (Illumina610quad) | | Singapore Chinese (Illumina1Mduov3) | | Singapore Malay | |
|---|---|---|---|---|---|---|
| Characteristics | T2D Patients | Controls | T2D Patients | Controls | T2D Patients | Controls |
| n | 1082 | 1006 | 928 | 939 | 794 | 1240 |
| (male/female) | (402/680) | (217/789) | (602/326) | (599/340) | (405/389) | (645/595) |
| Age (years) | — | 47.7 ± 11.1 | — | 46.7 ± 10.2 | 62.3 ± 9.9 | 56.9 ± 13.4 |
| Age-at-diagnosis (year) | 55.7 ± 12.0 | — | 52.2 ± 14.4 | — | — | — |
| Disease duration (years) | — | — | — | — | — | — |
| Body mass index (kg/m$^2$) | 25.3 ± 3.9 | 22.3 ± 3.7 | 25.4 ± 3.8 | 22.8 ± 3.4 | 27.8 ± 4.9 | 25.1 ± 4.8 |
| HbA$_{IC}$ (%) | — | — | — | — | 8.1 ± 1.8 | 5.6 ± 0.3 |
| Fasting plasma glucose (mmol/l) | — | 4.7 ± 0.45 | — | 4.7 ± 0.5 | — | — |

Data are shown as mean = SD or median (interquartile range).

TABLE S5

Meta-analysis of DACH1 rs1408888 with Type 2 diabetes in independent Asian cohorts.

| | n | | | Risk allele frequency | | OR | |
|---|---|---|---|---|---|---|---|
| Study | T2D | Control | Total | T2D | Control | (95% CI) | P |
| Hong Kong | 1567 | 1586 | 3153 | 0.753 | 0.716 | 1.21 | 9.1E−04 |
| Shanghai | 1779 | 1833 | 3612 | 0.763 | 0.761 | 1.01 | 0.8504 |
| Korean | 749 | 616 | 1365 | 0.560 | 0.596 | 0.96 | 0.6577 |
| Singapore | 2010 | 1945 | 3955 | 0.762 | 0.747 | 1.09 | 0.1058 |
| Singapore | 794 | 1240 | 2034 | 0.673 | 0.673 | 0.98 | 0.7810 |
| Japanese | 471 | 582 | 1053 | 0.666 | 0.647 | 1.09 | 0.3377 |
| Asian meta- | 7370 | 7802 | 15172 | — | — | 1.07 | 0.0112 |
| Heterogeneity | | | | | | | 0.1070 |

TABLE S6

Clinical characteristics and biochemical profile at baseline and allele frequency of DACH1 rs1408888 stratified according to the development of cardiovascular disease in 4296 Chinese T2D patients after a median follow up period of 8 years.

|  | Cardiovascular disease | | |
|---|---|---|---|
|  | No (n = 3714) | Yes (n = 582) | P |
| Clinical characteristics | | | |
| Sex (male/female) | 1617/2097 | 285/297 | |
| Male (%) | 43 | 49 | 0.014 |
| Age (years) | 54.1 ± 13.2 | 62.6 ± 11.0 | <.0001 |
| Age of diagnosis (years) | 47.9 ± 12.6 | 53.2 ± 12.2 | <.0001 |
| Duration of diabetes (years) | 6.2 ± 6.3 | 9.4 ± 7.2 | <.0001 |
| Follow-up period (years) | 8.9 ± 3.0 | 4.6 ± 3.1 | <.0001 |
| Smoking | | | 0.0001 |
| Non-smokers | 68.5% | 59.1% | |
| Ex smokers | 12.4% | 17.1% | |
| Current smokers | 19.1% | 23.8% | |
| Alcohol | | | 0.0270 |
| Non-alcohol users | 81.6% | 77.4% | |
| Ex alcohol users | 10.8% | 15.0% | |
| Current alcohol users | 7.62% | 7.60% | |
| BMI (kg/m$^2$) | 25.1 ± 4.1 | 25.1 ± 3.6 | 0.939 |
| Waist circumference (cm) | | | |
| Male | 87.9 ± 9.9 | 88.8 ± 8.6 | 0.1156 |
| Female | 83.2 ± 10.0 | 85.2 ± 9.8 | 0.0013 |
| HbA1c (%) | 7.6 ± 1.8 | 8.2 ± 1.9 | <.0001 |
| Total cholesterol (mmol/l) | 5.2 ± 1.1 | 5.4 ± 1.1 | <.0001 |
| Triglyceride (mmol/l) | 1.3 (0.9-1.9) | 1.4 (1.0-2.0) | 0.0007 |
| HDL-cholesterol (mmol/l) | 1.32 ± 0.36 | 1.25 ± 0.32 | <.0001 |
| LDL-cholesterol (mmol/l) | 3.2 ± 0.9 | 3.4 ± 1.0 | <.0001 |
| Systolic blood pressure | 133.4 ± 20.0 | 141.5 ± 20.6 | <.0001 |
| Diastolic blood pressure | 76.0 ± 10.7 | 77.3 ± 11.7 | 0.0102 |
| Sensory neuropathy (%) | 21.2% | 34.9% | <.0001 |
| Retinopathy (%) | 21.9% | 41.9% | <.0001 |
| ACR (mg/mmol) | 1.7 (0.7-7.2) | 5.6 (1.5-35.0) | <.0001 |
| eGFR (min/ml per 1.73 m$^2$) | 110.0 (89.7-131.0) | 94.4 (71.9-115.1) | <.0001 |
| Treatment | | | |
| Lipid lowering | 10.6% | 11.7% | 0.4482 |
| Blood pressure lowering | 37.6% | 50.7% | <.0001 |
| ACE inhibitors | 18.6% | 24.6% | 0.0007 |
| blood glucose lowering (oral drugs) | 63.9% | 64.8% | 0.6798 |
| Insulin | 14.2% | 22.9% | <.0001 |
| Allele/genotype frequencies | | | |
| rs1408888 (G/T) | 0.268/0.732 | 0.247/0.753 | 0.125 |
| GG/TG/TT genotypes | 0.072/0.392/0.536 | 0.047/0.400/0.553 | |

Data are shown as %, n, mean ± SD or median (interquartile range). BMI: body mass index; HbA$_{1c}$: glycated haemoglobin; HDL-cholesterol: high density lipoprotein-cholesterol; LDL-cholesterol: low density lipoprotein-cholesterol; ACR: albumin to creatinine ratio; eGFR: estimated glomerular filtration rate; ACE inhibitors: Angiotensin-converting enzyme inhibitors.

TABLE S7

Genotype distributions of DACH1 rs1408888 and hazard ratio of DACH1 rs1408888 for risk of cardiovascular disease.

| SNP | Location | Risk/non-risk allele | Event (N = 582) NN/NR/RR genotype frequencies | Control (N = 3714) NN/NR/RR genotype frequencies | Additive | | Dominant | | Recessive | |
|---|---|---|---|---|---|---|---|---|---|---|
| | | | | | P | HR (95% C.I.) | P | HR (95% C.I.) | P | HR (95% C.I.) |
| rs1408888 | Intron | T/G | 0.047/0.400/0.553 | 0.072/0.392/0.536 | 0.1621 | 1.10 (0.96-1.26) | 0.0451 | 1.49 (1.01-2.19) | 0.4712 | 1.06 |

Hazard ratios refer to the at-risk alleles. P values were calculated from Cox proportional hazard regression adjusted for conventional risk factors (sex, age and duration of diabetes, use of alcohol and tobacco, waist circumference, HbA$_{1c}$, LDL-cholesterol, HDL-cholesterol, natural logarithm of triglyceride, systolic and diastolic blood pressure, natural logarithm of eGFR, natural logarithm of ACR, retinopathy (present/absent), sensory neuropathy (present/absent), use of drugs (yes/no)) at baseline.

TABLE S8

Association of rs17252745, rs17252752 and rs57143718 with type 2 diabetes in the resequencing study.

| SNP | Position (bp) | Major/minor Alleles* | Minor allele frequency (n) Diabetic | Minor allele frequency (n) Nondiabetic | OR (95% CI) | P-Value |
|---|---|---|---|---|---|---|
| rs17252745 | 72426696 | T/G | 0.401 (438) | 0.441 (263) | 1.18 (0.94-1.46) | 0.1487 |
| rs17252752 | 72426823 | C/A | 0.413 (436) | 0.444 (266) | 1.17 (0.94-1.45) | 0.1742 |
| rs57143718 | 72427859 | T/C | 0.393 (459) | 0.450 (269) | 1.26 (1.02-1.56) | 0.0359 |

*The allele at risk is in Bold.

HM, Please give details for SNPs detected in the sequencing experiments and SNP frequency and OR in stage 1 (GWAS) and replication cohorts (YDM-control), I thought all 3 SNPs were positive in the 1st stage with 1 positive in the 2nd stage

TABLE S9

Summary of bioinformatics analysis of rs1408888 of DACH1.

| Feature | Position (hg18) | Result | Notes |
|---|---|---|---|
| rs1408888 | Chr13: 71326648 | T/G polymorphism | |
| GC % (±250 bp) | Chr13: 71326148-71327148 | 33.8% | |
| CpG island (±250 bp) | Chr13: 71326148-71327148 | No | |
| Transcription factor binding sites (±250 bp) | Chr13: 71326148-71327148 | With 5% dissimilarity allowed, 31 TF binding sites were identified in the rs1408888 ±250 bp region; TFIID and FOXP3 binding sites are common for both alleles. HNF-1A binding site is unique for T-allele; TBP, GR and C/EBPβ binding sites are unique for the G-allele. | Analysis by PROMO 3.0 (website: alggen.lsi.upc.es/cgi-bin/promo_v3/promo/promoinit.cgi?dirDB=TF_8.3) using TRANSFAC (website: gene-regulation.com/pub/databases.html#transfac) v.8.3 |
| FAIRE peaks | Chr13: 71326332-71326759 | Peak point 71326503; Score 637; SignalValue 0.017; P-value 0.063 145 bp away from rs1408888 with a peak of pancreatic islets FAIRE signal | Giresi and Lieb Methods. (2009) 48: 233-9. |
| DNaseI hypersensitive site | | No | Stitzel, M L. et al. Cell Metab. (2010) 12: 443-55. |
| Open chromatin (H3K4me3 association) | Chr13: 71335703-71340218 | 9 Kb downstream from rs1408888 | Stitzel, M. L. et al. Cell Metab. (2010) 12: 443-55. |
| CTCF binding sites | Chr13: 71351271-71351803 | About 25 Kb downstream from rs1408888 | Stitzel, M. L. et al. Cell Metab. (2010) 12: 443-55. |
| Islet-selective Clusters of Open Regulatory Elements (COREs) | Chr13: 70910039-71343328 | Lies on the 433 Kb islet FAIRE CORE | Gaulton, K. J. et al. Nature Genet. (2010) 42: 255-61. |
| Transcriptional module predicted by PReMod | Chr13: 71326382-71327308 | 4 modules predicted by PReMod in the vicinity of rs1408888 and one of them (mod030758) overlaps with rs1408888 region | Blanchette, M. et al. Genome Res. (2006) 16: 656-68. Website: genomequebec.mcgill.ca/PReMod/welcome |
| Conserved non-coding elements (CNE) | Chr13: 71324946-71325262 (hg18) | 1.5 kb upstream from rs1408888 with highly conserved non-coding element (CNE803) | Woolfe, A. et al. PLoS Biology (2005) 3: e7. |
| Regulatory elements | Chr13: 71323788-71326336 | OREG0002711 is 312 bp from rs1408888 | Open regulatory annotation database Website: oreganno.org/oregano/ |
| Copy number variation (CNV) | Chr13: 71226326-71383406 | rs1408888 lies on the 15 Kb CNV Variation_3912 | Redon R. et al. Nature (2006) 444: 444-54. Website: projects.tcag.ca/variation/?source=hg18 |
| microRNA | Chr13: 65690383-65690457 | hsa-mir-4704 is the closest microRNA 5.6 Mb from rs1408888 | |

Abbreviations: CTCF, CCCTC-binding factor, a DNA binding factor involved in gene insulation activity; FAIRE, Formaldehyde assisted isolation of regulatory elements, a technique which isolates DNA elements with open chromatins; FAIRE-CORE, Cluster of open regulatory elements isolated by the FAIRE technique; TFIID, transcription factor IID, a core component for transcription initiation; FOXP3, a forkhead box protein P3, a zinc finger transcription factor; HNF-1A, hepatic nuclear factor 1α, a homeo domain transcription factor; GR, glucocorticoid receptor, a zinc finger transcription factor; TBP, TATA-binding protein, binds to the TATA-box at the promoter; C/EBPβ, CCAAT/enhancer-binding protein β, a transcription factor binds to the CCAAT sequence to enhance gene expression.

TABLE S10

Associations of genetic variants of DACH1 with type 2 diabetes and other diseases in published studies.

| SNP | Position | Position in DACH1 gene | Distance to rs1408888 | $R^2$ to rs1408888 | D' to rs1408888 | CEU MAF | CHB MAF | Association | OR | P value | Ref |
|---|---|---|---|---|---|---|---|---|---|---|---|
| rs1408888 | Chr13: 71326648 | Intron 1 | 0 | 1 | 1 | 0.214 | 0.232 | T2D | 1.21 | $9.1 \times 10^{-4}$ | Current study |
| rs626277 | Chr13: 71245697 | Intron 1 | 80971 | 0 | 0.19 | 0.619 | 0.122 | T2D | 1.24 | 0.450 | Current study |
| rs626277 | Chr13: 71245697 | Intron 1 | 80971 | 0 | 0.19 | 0.619 | 0.122 | eGFRcrea | NA | $2.5 \times 10^{-11}$ | [1] |
| rs626277 | Chr13: 71245697 | Intron 1 | 80971 | 0 | 0.19 | 0.619 | 0.122 | CKD | 0.94 | $4.7 \times 10^{-3}$ | [1] |
| rs7991293 | Chr13: 71052876 | Intron 3 | 273772 | 0 | 0.067 | 0.076 | 0.012 | T2D | 1.469 | 0.019 | [2, 3] |
| rs7991293 | Chr13: 71052876 | Intron 3 | 273772 | 0 | 0.067 | 0.076 | 0.012 | T2D | NA | 0.010 | [2, 4] | eGFRcrea: glomerular filtration rate estimated by serum creatinine;
CKD: chronic kidney disease;
T2D: type 2 diabetes.
Reference:
[1] Kottgen, A. et al. Nat. Genet. (2010) 42: 376-84;
[2] Dreja, T. et al., Diabetologia, (2010) 53: 309-20;
[3] Saxena, R. et al., Science (2007) 316: 1331-6;
[4] Zeggini, E. et al., Science, (2007) 316: 1336-41.

TABLE S11

Quality control for inclusion of participants in stage 1.

|  | Controls | Cases |
|---|---|---|
| Number of subjects before QC | 102 | 100 |
| Exclusion criteria: |  |  |
| Duplicate | 0 | 0 |
| Gender inconsistency | 1 | 1 |
| Overall call rate <0.95 | 0 | 0 |
| population stratification | 0 | 0 |
| Number of subjects after QC | 101 | 99 |

What is claimed is:

1. A method for assessing the presence or risk of type 2 diabetes or cardiovascular disease in a human subject, comprising the steps of:
   (a) amplifying nucleotide sequence of a portion of genomic sequence of DACH1 (Dachshund homolog 1) present in a biological sample taken from the subject using primers consisting of SEQ ID NO:4 and SEQ ID NO:5,
   (b) detecting a T allele of polymorphism rs1408888 in the portion of genomic sequence of DACH1, and
   (c) determining that the subject has or is at risk of developing type 2 diabetes or cardiovascular disease.

2. The method of claim 1, wherein the sample is a blood or saliva sample.

3. The method of claim 1, wherein the subject has a BMI greater than 27 kg/m$^2$ and/or waist greater than 90 cm if the subject is a man or greater than 80 cm if the subject is a woman.

4. The method of claim 1 wherein the subject has a BMI less than 20 kg/m$^2$.

5. The method of claim 1, wherein the subject is younger than 20 years old.

6. The method of claim 1, wherein the subject was diagnosed of diabetes at an age younger than 40 years old and is assessed for the presence or risk of developing cardiovascular disease.

7. The method of claim 1, wherein the subject has a family history of type 2 diabetes or cardiovascular disease but has not been diagnosed of type 2 diabetes or cardiovascular disease.

8. The method of claim 1, wherein the amplification reaction is a polymerase chain reaction (PCR).

9. The method of claim 1, wherein the cardiovascular disease is coronary arteriosclerosis.

10. The method of claim 1, wherein, when the subject is indicated as having or at risk of developing type 2 diabetes or cardiovascular disease, further comprising the step of administering to the subject a cholesterol lowering drug or a blood glucose lowering drug.

11. The method of claim 1, wherein the polymorphism rs1408888 detected in step (c) is a TT genotype.

* * * * *

SEQUENCE LISTING

```
<160> NUMBER OF SEQ ID NOS: 17

<210> SEQ ID NO 1
<211> LENGTH: 254
<212> TYPE: DNA
<213> ORGANISM: Takifugu rubripes
<220> FEATURE:
<223> OTHER INFORMATION: conserved non-vertebrate non-coding sequence
      element ID CNE803, conserved non-coding element (CNE), Fugu CNE803

<400> SEQUENCE: 1
actttttaag gattccagcc ttgtcatttt caattttctg ctctttggac atgcttgtat      60
tcagattccc caacatctat tcgccatatc aatcctaatt agacaatctg ggagcacgaa     120
gggtgggagc agctttattt gcataattta atcataaata ctcagtgata catatttcca     180
aatgcatttg tacaattatc ttttcttcct tggggcaaaa gtattaatat gattaggcaa     240
taattcttta aaaa                                                       254

<210> SEQ ID NO 2
<211> LENGTH: 255
<212> TYPE: DNA
<213> ORGANISM: Homo sapiens
<220> FEATURE:
<223> OTHER INFORMATION: human sequence corresponding to conserved
      non-vertebrate non-coding sequence element ID CNE803, conserved
      non-coding element (CNE), Fugu CNE803

<400> SEQUENCE: 2
acttttcttt ggatttcagc cttgtcattt ccaattttct gctccttgga catgcttgta      60
ttcaaattct ggaacatcta ttcagcatat caatcctaat tagacaatct gggtctggaa     120
```

-continued

```
aggatgagag ctgggtcatt tgcataattt aatcataaat actcagtgat acatatttcc    180
aaatgcattt gtacaattat cttttcatcc ttggggcaat ggtattaata tgattaggca    240
atatttctgg aaaaa                                                     255

<210> SEQ ID NO 3
<211> LENGTH: 141
<212> TYPE: DNA
<213> ORGANISM: Homo sapiens
<220> FEATURE:
<223> OTHER INFORMATION: human eye EST BY797940, cDNA clone HE2999.seq
      5-

<400> SEQUENCE: 3
ctggaaagga tgagagctgg gtcatttgca taatttaatc ataaatactc agtgatacat    60
atttccaaat gcatttgtac aattatcttt tcatccttgg gcaatggta ttaatatgat    120 taggcaatat ttctggaaaa a                                              141

<210> SEQ ID NO 4
<211> LENGTH: 26
<212> TYPE: DNA
<213> ORGANISM: Artificial Sequence
<220> FEATURE:
<223> OTHER INFORMATION: synthetic PCR amplification primer DACH1-F

<400> SEQUENCE: 4
tcttgctata aaatgcatga aaggag                                         26

<210> SEQ ID NO 5
<211> LENGTH: 20
<212> TYPE: DNA
<213> ORGANISM: Artificial Sequence
<220> FEATURE:
<223> OTHER INFORMATION: synthetic PCR amplification primer 1R

<400> SEQUENCE: 5
atagccaaag ggagggaaaa                                                20

<210> SEQ ID NO 6
<211> LENGTH: 20
<212> TYPE: DNA
<213> ORGANISM: Artificial Sequence
<220> FEATURE:
<223> OTHER INFORMATION: synthetic 1.7 Kb DNA fragmet sequencing primer
      1F

<400> SEQUENCE: 6
aagggcccat gacaggaatg                                                20

<210> SEQ ID NO 7
<211> LENGTH: 23
<212> TYPE: DNA
<213> ORGANISM: Artificial Sequence
<220> FEATURE:
<223> OTHER INFORMATION: synthetic 1.7 Kb DNA fragmet sequencing primer
      3F

<400> SEQUENCE: 7
tcactcaaga tgagttcaca cca                                            23

<210> SEQ ID NO 8
<211> LENGTH: 20
<212> TYPE: DNA
<213> ORGANISM: Artificial Sequence
```

-continued

<220> FEATURE:
<223> OTHER INFORMATION: synthetic 1.7 Kb DNA fragmet sequencing primer 2R

<400> SEQUENCE: 8
gttattatcg gcccaattcc                                               20

<210> SEQ ID NO 9
<211> LENGTH: 20
<212> TYPE: DNA
<213> ORGANISM: Artificial Sequence
<220> FEATURE:
<223> OTHER INFORMATION: synthetic PCR amplification primer CNE803-1F

<400> SEQUENCE: 9
taataccatt gccccaagga                                               20

<210> SEQ ID NO 10
<211> LENGTH: 21
<212> TYPE: DNA
<213> ORGANISM: Artificial Sequence
<220> FEATURE:
<223> OTHER INFORMATION: synthetic PCR amplification primer DACH1-R

<400> SEQUENCE: 10
cagcaaatcc cagcgtagca c                                             21

<210> SEQ ID NO 11
<211> LENGTH: 20
<212> TYPE: DNA
<213> ORGANISM: Artificial Sequence
<220> FEATURE:
<223> OTHER INFORMATION: synthetic sequencing primer CNE803-2F

<400> SEQUENCE: 11
tgacccagct ctcatccttt                                               20

<210> SEQ ID NO 12
<211> LENGTH: 20
<212> TYPE: DNA
<213> ORGANISM: Artificial Sequence
<220> FEATURE:
<223> OTHER INFORMATION: synthetic PCR detection primer for CNE expression

<400> SEQUENCE: 12
taataccatt gccccaagga                                               20

<210> SEQ ID NO 13
<211> LENGTH: 20
<212> TYPE: DNA
<213> ORGANISM: Artificial Sequence
<220> FEATURE:
<223> OTHER INFORMATION: synthetic PCR detection primer for CNE expression

<400> SEQUENCE: 13
tttggatttc agccttgtca                                               20

<210> SEQ ID NO 14
<211> LENGTH: 20
<212> TYPE: DNA
<213> ORGANISM: Artificial Sequence
<220> FEATURE:
<223> OTHER INFORMATION: synthetic PCR detection primer for DACH1 expression

```
-continued

<400> SEQUENCE: 14
ctgcaccaac gcaagttcta                                              20

<210> SEQ ID NO 15
<211> LENGTH: 20
<212> TYPE: DNA
<213> ORGANISM: Artificial Sequence
<220> FEATURE:
<223> OTHER INFORMATION: synthetic PCR detection primer for DACH1
      expression

<400> SEQUENCE: 15
ataagcccat cagcatctgg                                              20

<210> SEQ ID NO 16
<211> LENGTH: 20
<212> TYPE: DNA
<213> ORGANISM: Artificial Sequence
<220> FEATURE:
<223> OTHER INFORMATION: synthetic PCR detection primer for beta-actin
      expression positive control

<400> SEQUENCE: 16
agagctacga gctgcctgac                                              20

<210> SEQ ID NO 17
<211> LENGTH: 20
<212> TYPE: DNA
<213> ORGANISM: Artificial Sequence
<220> FEATURE:
<223> OTHER INFORMATION: synthetic PCR detection primer for beta-actin
      expression positive control

<400> SEQUENCE: 17
agcactgtgt tggcgtacag                                              20
```